(12) United States Patent
Hettrick et al.

(10) Patent No.: US 12,226,220 B2
(45) Date of Patent: *Feb. 18, 2025

(54) SYSTEMS AND METHODS FOR ASSESSING SYMPATHETIC NERVOUS SYSTEM TONE FOR RENAL NEUROMODULATION THERAPY

(71) Applicant: Medtronic Ireland Manufacturing Unlimited Company, Dublin (IE)

(72) Inventors: Douglas Hettrick, Andover, MN (US); Shantanu Sarkar, Roseville, MN (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,426

(22) Filed: Jun. 1, 2023

(65) Prior Publication Data

US 2023/0309902 A1 Oct. 5, 2023

Related U.S. Application Data

(63) Continuation of application No. 16/885,574, filed on May 28, 2020, now Pat. No. 11,707,220, which is a
(Continued)

(51) Int. Cl.
*A61B 5/00* (2006.01)
*A61B 5/024* (2006.01)
(Continued)

(52) U.S. Cl.
CPC .......... *A61B 5/4035* (2013.01); *A61B 5/0245* (2013.01); *A61B 18/1492* (2013.01);
(Continued)

(58) Field of Classification Search
CPC . A61B 5/4035; A61B 5/0245; A61B 18/1492; A61B 5/00; A61B 5/02405; A61B 5/053; A61B 5/349; A61B 5/4836; A61B 2018/00404; A61B 2018/00434; A61B 2018/00511; A61B 2018/00773; A61B 2018/00839; A61B 2018/00875; A61B 2018/0212; A61B 2018/0262;
(Continued)

(56) References Cited

U.S. PATENT DOCUMENTS 10,004,458 B2 * 6/2018 Toth .......................... A61N 1/05
10,667,736 B2 * 6/2020 Hettrick ................. G16H 50/20
(Continued)

*Primary Examiner* — Jonathan T Kuo
(74) *Attorney, Agent, or Firm* — Shumaker & Sieffert, P.A.

(57) ABSTRACT

Systems and methods for assessing sympathetic nervous system (SNS) tone for renal neuromodulation therapy are disclosed herein. A system configured in accordance with embodiments of the present technology can include, for example, a detector attached to or implanted in a patient and a receiver communicatively coupled to the detector. The detector can measure cardiac data and the receiver and/or a device communicatively coupled thereto can analyze the cardiac data to provide one or more SNS tone indicators. The SNS tone indicators can be used to determine whether a patient will be responsive to a neuromodulation therapy and/or whether a neuromodulation therapy was effective.

19 Claims, 13 Drawing Sheets

Related U.S. Application Data continuation of application No. 15/526,472, filed as application No. PCT/US2015/066469 on Dec. 17, 2015, now Pat. No. 10,667,736.

(60) Provisional application No. 62/093,933, filed on Dec. 18, 2014, provisional application No. 62/093,383, filed on Dec. 17, 2014.

(51) Int. Cl.
*A61B 5/0245* (2006.01)
*A61B 5/053* (2021.01)
*A61B 18/00* (2006.01)
*A61B 18/02* (2006.01)
*A61B 18/14* (2006.01)
*A61B 34/00* (2016.01)
*A61N 1/36* (2006.01)
*A61N 7/02* (2006.01)
*G16H 20/17* (2018.01)
*G16H 20/30* (2018.01)
*G16H 20/40* (2018.01)
*G16H 50/20* (2018.01)
*G16H 50/30* (2018.01)

(52) U.S. Cl.
CPC ......... *A61N 1/36017* (2013.01); *G16H 20/30* (2018.01); *G16H 20/40* (2018.01); *G16H 50/20* (2018.01); *G16H 50/30* (2018.01); *A61B 5/00* (2013.01); *A61B 5/02405* (2013.01); *A61B 5/053* (2013.01); *A61B 5/4836* (2013.01); *A61B 2018/00404* (2013.01); *A61B 2018/00434* (2013.01); *A61B 2018/00511* (2013.01); *A61B 2018/00773* (2013.01); *A61B 2018/00839* (2013.01); *A61B 2018/00875* (2013.01); *A61B 2018/0212* (2013.01); *A61B 2018/0262* (2013.01); *A61B 2018/1435* (2013.01); *A61B 2034/256* (2016.02); *A61N 7/022* (2013.01); *G16H 20/17* (2018.01)

(58) Field of Classification Search
CPC ...... A61B 2018/1435; A61B 2034/256; A61N 1/36017; A61N 7/022; G16H 20/30; G16H 20/40; G16H 20/17; G16H 50/00–50/80

See application file for complete search history.

(56) References Cited

U.S. PATENT DOCUMENTS

| | | | |
|---|---|---|---|
| 11,707,220 B2 * | 7/2023 | Hettrick | G16H 20/30 600/301 |
| 2014/0288551 A1 * | 9/2014 | Bharmi | A61N 1/36121 606/41 |
| 2016/0029960 A1 * | 2/2016 | Toth | A61N 1/36139 606/41 |

* cited by examiner

SYSTEMS AND METHODS FOR ASSESSING SYMPATHETIC NERVOUS SYSTEM TONE FOR RENAL NEUROMODULATION THERAPY

CROSS-REFERENCE TO RELATED APPLICATION(S)

This application is a continuation of U.S. patent application Ser. No. 16/885,574, titled "SYSTEMS AND METHODS FOR ASSESSING SYMPATHETIC NERVOUS SYSTEM TONE FOR RENAL NEUROMODULATION THERAPY," filed on May 28, 2020, which is a continuation of U.S. patent application Ser. No. 15/526,472, titled "SYSTEMS AND METHODS FOR ASSESSING SYMPATHETIC NERVOUS SYSTEM TONE FOR NEUROMODULATION THERAPY," filed on May 12, 2017 and issued as U.S. Pat. No. 10,667,736 on Jun. 2, 2020, which claims the benefit of and is a U.S. National Stage entry under 35 U.S.C. § 371 of International Application No. PCT/US2015/066469, titled "SYSTEMS AND METHODS FOR ASSESSING SYMPATHETIC NERVOUS SYSTEM TONE FOR RENAL NEUROMODULATION THERAPY," filed Dec. 17, 2015, which claims the benefit of U.S. Provisional Patent Application No. 62/093,933, titled "SYSTEMS AND METHODS FOR ASSESSING SYMPATHETIC NERVOUS SYSTEM TONE FOR RENAL NEUROMODULATION THERAPY," filed on Dec. 18, 2014, and U.S. Provisional Patent Application No. 62/093,383, titled "SYSTEMS AND METHODS FOR ASSESSING SYMPATHETIC NERVOUS SYSTEM TONE FOR RENAL NEUROMODULATION THERAPY," filed on Dec. 17, 2014, all of which are incorporated herein by reference in their entireties.

TECHNICAL FIELD

The present technology is related to neuromodulation therapy. In particular, various embodiments of the present technology are related to systems and methods for assessing sympathetic nervous system ("SNS") tone before and after renal neuromodulation therapy.

BACKGROUND

The SNS is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
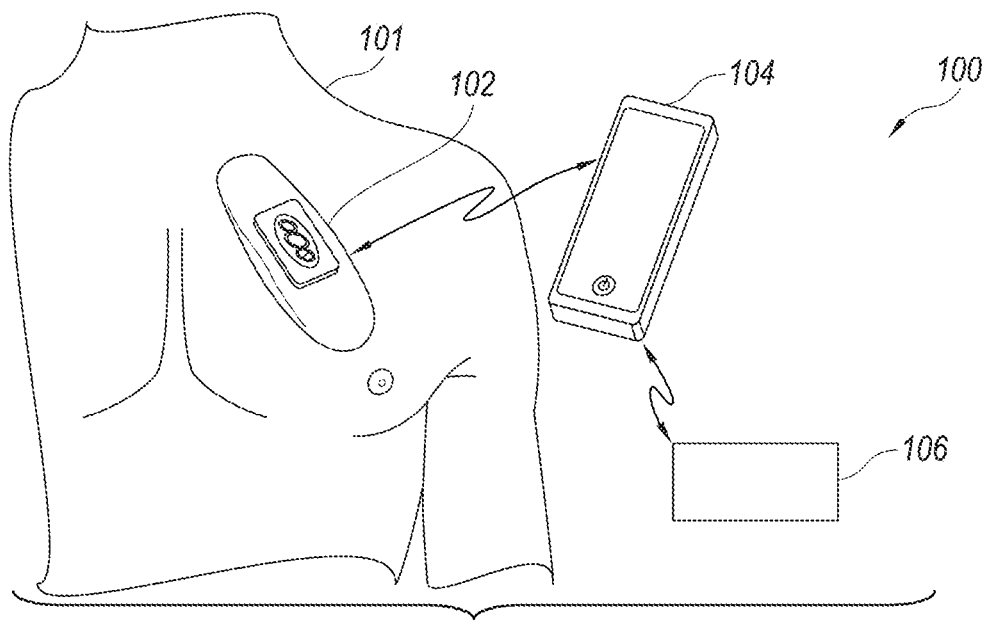
FIG. 1 is a partially schematic illustration of a monitoring system for detecting SNS tone indicators configured in accordance with an embodiment of the present technology.

Systems and methods in accordance with embodiments of the present technology can be configured assess SNS tone for renal neuromodulation therapy. Assessing a patient's basal SNS tone (also referred to as "sympathetic tone") expected to indicate whether a patient will be receptive to renal neuromodulation or other autonomic modulation therapies. In addition, assessing SNS tone after renal neuromodulation therapy is expected to indicate whether the sufficient neuromodulation has occurred to provide the desired therapeutic effect (e.g., a drop in blood pressure). Specific details of several embodiments of the present technology are described herein with reference to FIGS. 1-16. Although many of the embodiments are described with respect to devices, systems, and methods for intravascular renal neuromodulation, other applications and other embodiments in addition to those described herein are within the scope of the present technology. For example, at least some embodiments of the present technology may be useful for intraluminal neuromodulation, for extravascular neuromodulation, for non-renal neuromodulation, and/or for use in autonomic modulation therapies other than neuromodulation.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

I. SELECTED EMBODIMENTS OF SYSTEMS FOR ASSESSING SNS TONE AND ASSOCIATED METHODS

Renal neuromodulation therapy aims to modulate the autonomic nervous system, specifically the SNS, by modulating or destroying renal efferent sympathetic nerves and afferent renal sensory nerves. Accordingly, patients with elevated SNS tone are expected to be more responsive to renal neuromodulation therapy and other related therapies. Therefore, SNS tone can be used as an indicator of whether a patient is a good candidate for neuromodulation therapy. Additionally or alternatively, after neuromodulation therapy, SNS tone can serve as an indicator that the therapy has modulated the nerves to a degree sufficient to provide therapeutic effects (e.g., a reduction in blood pressure). Various diagnostic indices are associated with sympathetic tone. These indices include, for example, blood pressure, heart rate variability ("HRV"), night heart rate, day-night heart rate difference ("DND"), impedance variability, and combinations thereof.

FIG. 1 is a partially schematic illustration of a monitoring system 100 for detecting SNS tone indicators configured in accordance with an embodiment of the present technology. As shown in FIG. 1, the monitoring system 100 can include a detector 102 for measuring cardiac data and/or other detectable parameters of a patient 101 and a receiver 104 that receives the data detected by the detector 102. The detected data can be communicated to the receiver 104 using a wireless or wired connection (e.g., via a Bluetooth or cellular connection). The receiver 104 can then transmit the detected data to a remote location, such as a remote central processor or computer 106 (shown schematically). For example, the receiver 104 and the computer 106 can be wirelessly connected via an intranet or internet connection. The central computer 106 can process the received cardiac data to provide one or more diagnostic indices associated with sympathetic tone, such as HRV, night heart rate, and DND. In other embodiments, the receiver 104 itself may include a processor configured to analyze the data and provide the desired SNS tone indicators (e.g., HRV, DND, impedance variability, etc.). In further embodiments, the receiver 104 and the detector 102 can be integrated into a single device for measuring data, transmitting the detected data, and/or processing the detected data.

In embodiment illustrated in FIG. 1, the detector 102 is a wireless external patch that can be attached to the skin of a patient 101 for cardiac and/or other monitoring over a period of time. As shown in FIG. 1, for example, the detector 102 can be positioned on the patient's chest over or proximate to the patient's heart. The detector 102 can be attached to the patient's skin with an adhesive or other suitable attachment means. The detector 102 includes multiple electrodes (e.g., four electrodes; not shown) that can take bipolar and/or quadripolar measurements of the heart's electrical conduction system to provide electrocardiogram ("ECG") measurements and/or other electrical measurements associated with cardiac function. For example, the same electrodes can be used to take thoracic impedance measurements. These measurements can then be processed (e.g., via the computer 106 or the receiver 104) using algorithms to determine various indices associated with SNS tone, such as HRV, night heart rate, DND, impedance variability, baro-reflex variability, daily net duration of atrial tachyarrhythmias (e.g., an arrhythmia indicator), atria tachyarrhythmia/atrial fibrillation burden ("AT/AF burden"), and/or combinations thereof. In various embodiments, the detector 102 can include an accelerometer (e.g., a 3-D accelerometer) to quantify a patient's physical activity, which can include parameters like minutes or days above a minimal activity threshold, and can be expressed as an index of quality of life or as an activity indicator. In further embodiments, the detector 102 can include additional sensing devices that detect other physiological parameters, such as blood pressure, posture, temperature, and/or other indices that may be used to determine the SNS tone of the patient 101.

In certain embodiments, the external detector 102 can remain attached to the patient 101 for an extended period of time, such as 30 days, to continuously or intermittently monitor the patient's cardiac data over that period of time.

In other embodiments, the external detector 102 can be configured to remain attached to the patient for shorter periods of time (e.g., 5 days, 10 days, 15 days, etc.) or longer periods of time (e.g., 45 days, 60 days, 120 days, etc.) depending on the desired monitoring period. It is expected that the extended monitoring of cardiac activity (e.g., HRV) serves as a better indicator of sympathetic tone than brief monitoring periods, such as an hour-long monitoring period or a 24-hour monitoring period that is typically associated with a standard Holter monitor). The extended monitoring can at least substantially average out abnormalities (e.g., atrial fibrillation) that may skew the cardiac measurements if the measurements were taken over a shorter period of time (e.g., several minutes, an hour, a day, etc.). In other embodiments, irregular cardiac measurements detected during the extended monitoring can be filtered out of the data used to determine the SNS tone indicator. For example, the extended monitoring period allows the user or the system 100 to identify and discriminate time periods of supraventricular arrhythmias (e.g., atrial fibrillation) when the SNS is not actually influencing heart rate. Suitable external detectors 102 include, for example, the SEEQ Mobile Cardiac Telemetry System from Medtronic, Inc. of Minneapolis, Minnesota.

Figure 2:
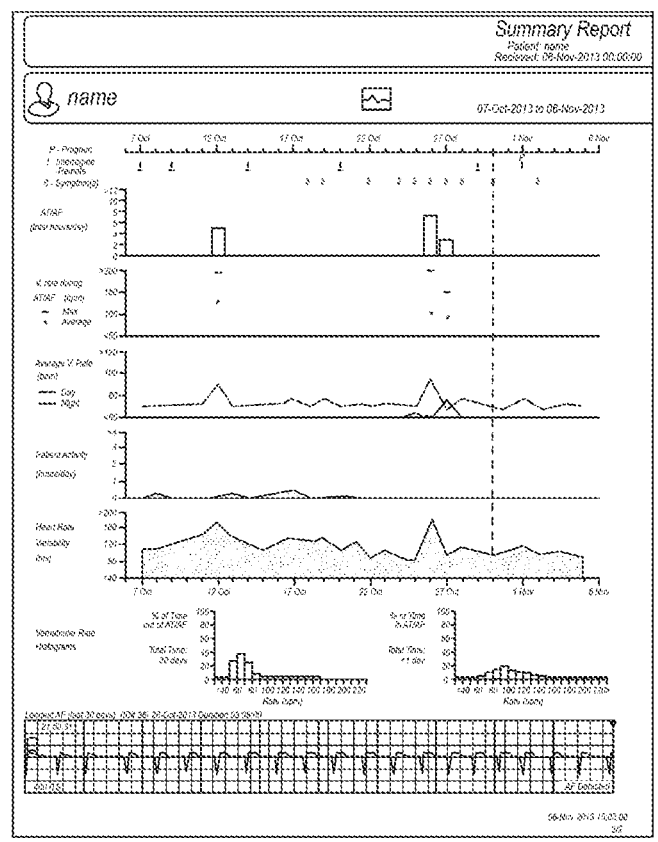
FIG. 2 is an illustration of a report provided by the monitoring system of FIG. 1 configured in accordance with an embodiment of the present technology.

Once the detected data has been converted to the desired SNS tone indicator (e.g., HRV), the information can be provided to a user (e.g., a clinician or a patient) to allow the user to assess the patient's basal SNS tone. In certain embodiments, the SNS indicator(s) can be displayed to the user on a monitor or other type of display at the central computer 106 and/or at a device remote from and communicatively connected to the central computer 106 (e.g., a personal computer, a tablet computer, a smartphone, and/or the receiver 104). FIG. 2 illustrates a display 208 with a report that can be provided to the user based on the received cardiac data. As shown in FIG. 2, the report can include a graph illustrating the patient's HRV over the course of a monitoring period. Measurements of various SNS tone indicators can be measured daily, intermittently throughout the day, and/or substantially continuously, and these measurements can then be combined into single parameters, such as mean, median, standard deviation, etc. In other embodiments, the display 208 can provide the user with one or more other or additional SNS tone indicators, such as the patient's night heart rate, DND, impedance variability, atrial tachyarrhythmia-atrial fibrillation ("AT-AF") burden (e.g., an arrhythmia detector), and/or combinations thereof. In further embodiments, the display 208 can provide the user with a parameter that takes into account a patient's daily activity (measured by an accelerometer; e.g., a quality of life index). In certain embodiments, the various SNS indicators can be combined into a single SNS tone score using empirical, Bayesian, multivariate, and/or other types of statistical analysis.

The SNS tone indicators can then be used to assess whether a patient is a good candidate for neuromodulation therapy and/or whether neuromodulation therapy has destroyed the nerves to a desired degree. For example, when the SNS tone indicator includes HRV, the patients HRV can be compared to a predetermined HRV range or value. This predetermined HRV range or value can be an absolute standardized value or determined empirically, and correspond to a normal HRV range or value for a healthy human patient, a normal HRV range or value for a patient with similar characteristics as the monitored patient, and/or another predetermined HRV value or range. Typically, elevated sympathetic tone is indicated by a lower HRV value than the normal HRV range. Accordingly, if the detected HRV value is lower than the predetermined I-IRV value, this may indicate that the patient has elevated sympathetic tone and will likely be receptive to neuromodulation therapy. Similarly, when DND and impedance variability are used as SNS tone indicators, measured DND and impedance variability values that am lower than threshold healthy DND and impedance variability values may be indicative of elevated sympathetic tone. Various manners of assessing impedance variability as it relates to autonomic nervous system health are disclosed in U.S. Pat. No. 8,435,186, issued May 7, 2013. When night heart rate is used as the SNS tone indicator, a measured night heart rate higher than a threshold range may be indicative of elevated sympathetic tone. Likewise, an average nighttime heart rate higher than an average daytime heart rate may be indicative of elevated sympathetic tone, regardless of actual night heart rate. High nighttime time blood pressure and nighttime activity may also be indicative of elevated sympathetic tone.

In other embodiments, multiple indices of changes in sympathetic tone (e.g., HRV, DND, and impedance variability) can be combined into a single integrated diagnostic parameter of SNS tone (e.g., an "SNS tone score") and compared to a predetermined value associated with a healthy SNS. For example, a point system could be ascribed to various SNS tone indicators such that HRV below a threshold HRV value would be worth X points, DND above a predetermined threshold DND value would be worth Y points, and/or other SNS tone indicators above/below a corresponding predetermined threshold value would be worth a certain number of points. Other indices may also be included in the SNS tone score, such as blood pressure, age, weight, body mass index ("BMI"), and/or pharmaceutical/drug intake, that may be indicative of sympathetic tone and responsiveness to neuromodulation therapy. When a patient's net total points (e.g., X+Y+ . . . N) is greater than a threshold integrated diagnostic value (e.g., Z), the patient would be considered a good candidate for renal neuromodulation therapy. The values of the SNS tone indicators (e.g., X and Y) and the integrated SNS tone indicator (e.g. Z) may be assigned empirically or determined based on clinical trial data. In certain embodiments, the integrated diagnostic parameter of SNS tone can be determined using algorithms that include Bayesian statistics, multivariate analysis, and/or other artificial intelligence strategies. In various embodiments, the system 100 can include algorithms that analyze the SNS indicators to automatically determine whether a patient has elevated sympathetic tone and is a good candidate for neuromodulation therapy, and provide this recommendation to the user via the central computer 106 and/or other computing device that is communicatively coupled to the monitoring system 100 and accessible by the user (e.g. a clinician, a patient, etc.).

In various embodiments, the monitoring system 100 (FIG. 1) can continue measuring and analyzing cardiac data after neuromodulation therapy. For example, the monitoring system 100 can continue to measure SNS tone indicators one month, three months, or six months after neuromodulation therapy. In other embodiments, the monitoring system 100 can detect the SNS tone indicators for longer or shorter periods of time. A lack change in autonomic indices or a lack of improvement in patient activity (i.e., an index of quality of life or an activity indicator as determined using an accelerometer) could indicate insufficient neuromodulation and the need to repeat the neuromodulation therapy to further ablate the nerves. For example, a patients blood pressure may not decrease after a neuromodulation therapy, which could indicate that the treatment was not successful, or, alternatively, that the patient was not a good candidate for neuromodulation therapy from the beginning. In this instance, the SNS tone indicators can be measured to determine whether the neuromodulation therapy has had an effect on the patient's sympathetic tone. If the SNS tone indicators show a decrease in the sympathetic tone, it can be indicative that the nerves are indeed ablated to the desired degree and that some other factor is contributing to the high blood pressure. For example, it could be that the effects of the neuromodulation have not yet fully taken effect to lower blood pressure or that the patient is behaving in a manner that is raising his or her blood pressure (e.g., changes in diet, activity level, prescriptions, etc.). Thus, the SNS indicators can provide a mechanism for determining whether a neuromodulation therapy was successful and whether the nerves need to be further ablated with a repeated neuromodulation treatment.

In other embodiments, the monitoring system 100 can be used to screen candidates for and/or assess the efficacy of other device-based treatments that lower blood pressure based on autonomic modulation. For example, the monitoring system 100 can be used to assess the SNS tone of patients before and/or after baroreceptor activation therapy, carotid body modulation, passive mechanical carotid baroreceptor stimulation (e.g., a nitinol stent), intrathecal clonidine infusion, and/or vagal nerve stimulation.

Figure 3A:
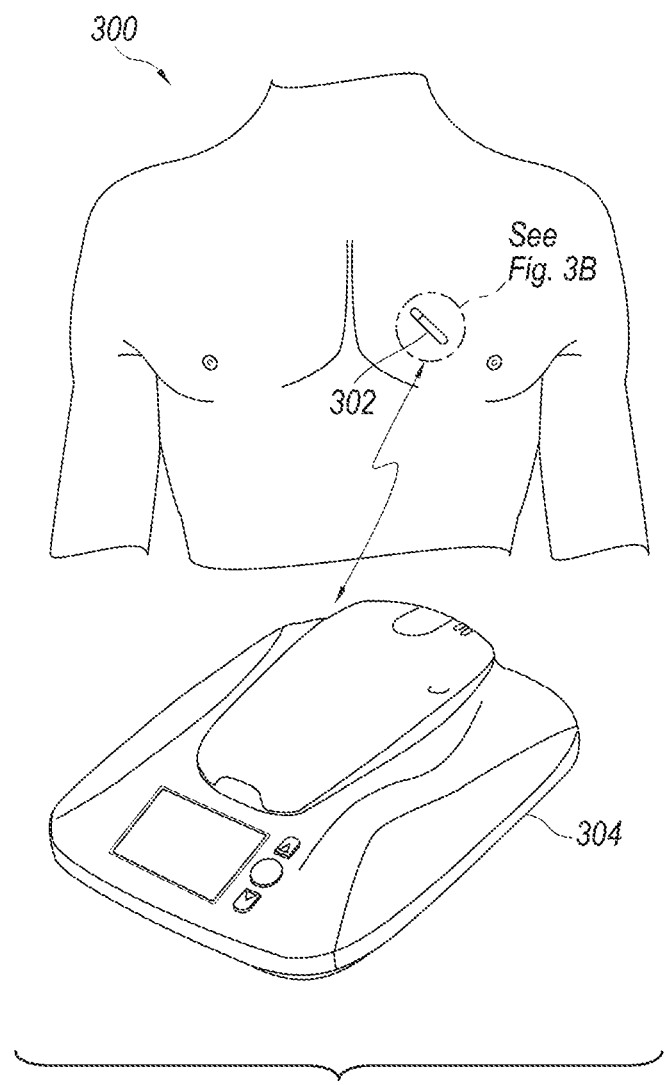
FIG. 3A is an illustration of a monitoring system for detecting SNS tone indicators configured in accordance with another embodiment of the present technology.
Figure 3B:
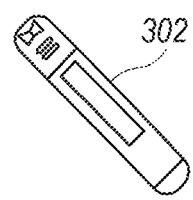
FIG. 3B is an illustration of a component of the monitoring system of FIG. 3A.

FIG. 3A is an illustration of a monitoring system 300 for detecting SNS tone indicators configured in accordance with an embodiment of the present technology. The monitoring system 300 can include various features generally similar to the features of the monitoring system 100 of FIG. 1. For example, the monitoring system 300 includes a detector 302 that measures cardiac activity (e.g., ECG data) and a receiver 304 communicatively connected to the detector 302 via a cellular, Bluetooth, and/or other wireless connection. Instead of the external detector 102 of FIG. 1, however, the detector 302 is implanted within a patient. FIG. 3B, for example, is an enlarged, partially schematic illustration of the detector 302 before implantation in the patient. Referring to FIGS. 3A and 3B together, the detector 302 can be subcutaneously implanted proximate to the patient's heart and provide long-term monitoring of the patient's cardiac and/or activity data before and/or after neuromodulation therapy. Suitable implantable detectors 302 include, for example, the Reveal LINQ Insertable Cardiac Monitoring System from Medtronic, Inc. of Minneapolis, Minnesota and the Reveal XT Insertable Cardiac Monitor from Medtronic, Inc. of Minneapolis, Minnesota.

The receiver 304 is adapted to receive the measured cardiac data from the detector 302 and can analyze the data to provide a user with one or more parameters associated with SNS tone. For example, the receiver 304 can provide HRV, DND, night heart rate, impedance variability, net AT/AF burden, patient daily activity, other diagnostic indices indicative of SNS tone, and/or combinations thereof. This information can be displayed on the receiver 304 itself and/or on a device communicatively coupled thereto (e.g., a personal computer, a tablet computer, a smart phone, a central computer, etc.). In other embodiments, the receiver 304 can be communicatively coupled to a remote device (e.g., the central computer 106 of FIG. 1, a central processing unit, etc.), and transmit the data measured by the detector 304 to the remote device where it can be analyzed to provide a clinician or other user with the SNS tone indicators.

The SNS tone indicators can include HRV, DND, night heart rate, impedance variability, other autonomic tone indices, and/or an integrated diagnostic parameter that combines two or more of the sympathetic tone indices. In other embodiments, the integrated diagnostic parameter can include other physiological parameters (e.g., blood pressure, gender, ethnic background, etc.) that may be indicative of sympathetic tone and responsiveness to neuromodulation therapy. Before therapy, the SNS tone indicator(s) can then be used to determine whether a patient has an elevated sympathetic tone and, therefore, will be receptive to renal neuromodulation therapy and/or other device-based therapies that lower blood pressure based on autonomic modulation. After autonomic modulation therapy, the SNS tone indicator(s) provided by the monitoring system 300 can be used to monitor the patient's SNS tone to determine whether the treatment was successful (e.g., ablated the nerves to a desired degree to decrease blood pressure).

Figure 4:
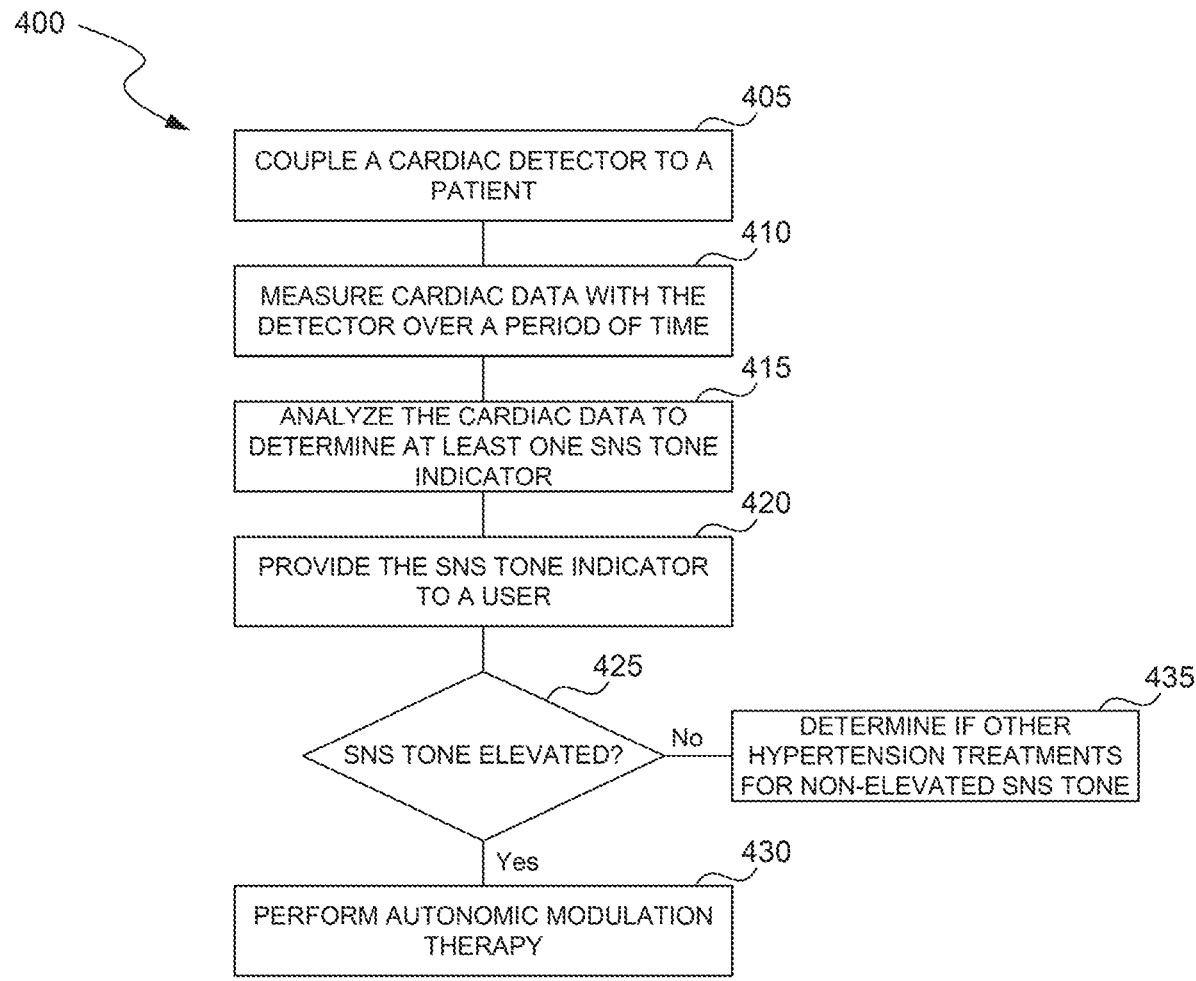
FIG. 4 is a block diagram illustrating a method of evaluating SNS tone for autonomic modulation therapy in accordance with an embodiment of the present technology.

FIG. 4 is a block diagram illustrating a method 400 of evaluating SNS tone for autonomic modulation therapy in accordance with an embodiment of the present technology. The method 400 can be implemented using the monitoring systems 100 and 300 described above with reference to FIGS. 1-3B and/or other suitable monitoring systems for determining SNS tone indicators. For example, the detectors 102, 302, the receivers 104, 304, and/or the central computer 106 can be used to perform various steps of the method 400. As shown in FIG. 4, the method 400 includes coupling a cardiac detector to a patient to record cardiac data (block 405). The cardiac detector can be an external device that is attached to the patient's skin (e.g., proximate to the patient's heart), or it can be an implantable device. The implantable device, for example, can be subcutaneously implanted proximate to the patient's heart, attached directly to the patient's heart, and/or otherwise implanted to record cardiac activity. The detector can include multiple electrodes to record ECG data and/or other electrical measurements associated with cardiac activity. In other embodiments, the detector can include different or additional sensors that record other information related to cardiac activity and/or other parameters that may be indicative of SNS tone, such as a 3-D accelerometer for measuring daily activity levels and a Holter monitor for measuring HRV data. In certain embodiments, the method 400 can be performed using detectors previously attached or implanted in the patient and configured to provide cardiac data and/or daily activity-type data. Once attached or implanted, the detector can measure cardiac and/or other data over a period of time (block 410). In certain embodiments, the detector can sense cardiac activity over several days, a month, a year, or longer. Extended monitoring beyond several years is also possible by appending stored diagnostic data from a detector previously used by the patient (and may have expired due to battery depletion) to a newly implanted or attached replacement detector with similar capabilities. In this manner, them is no upper limit for the monitoring period and the method 400 can include continuous monitoring of desired indices related to SNS tone.

After the monitoring period, the method 400 continues by analyzing the measured diagnostic cardiac data to determine at least one SNS tone indicator (block 415). Using equations, algorithms, and various statistical methods, the cardiac data recorded by the detector can be used to determine HRV, DND, night heart rate, impedance variability, net duration of AT-AF, patient activity levels (e.g., a quality of life index), and/or other parameters indicative of SNS tone. In other embodiments, the method 400 can provide an integrated diagnostic parameter of SNS tone based on one or more SNS indicators and/or additional physiological parameters that may have an effect on SNS tone. For example, the method 400 may use an algorithm executed by a processor to optimize the combination of two or more SNS indicators and/or other data to provide a parameter that is more closely tied to SNS tone than any one individual SNS tone indicator alone. In various embodiments, the detector can be communicatively coupled to a receiver (e.g., via a cellular or Bluetooth connection) that can perform the analysis of the data (e.g., via a processor) and/or transmit the cardiac data to a remote processor (e.g., at a central computer) that can analyze the cardiac data to provide SNS tone indicators.

One or more of the SNS tone indicators and/or an overall SNS tone score can then be provided to a user (e.g., a clinician) on a display (block 420). For example, the method 400 can provide a report that displays the SNS tone indicator (s) to the user on a smart phone, a computer, a tablet computer, and/or other device including a digital display. Similar to the display 208 of FIG. 2, the method 400 can display the SNS tone indicator(s) over the course of a monitoring period so that the user can assess the patient's SNS tone over that time. When the SNS tone indicator is viewed over the course of the monitoring period, the user may be able identify when patients have abnormalities that may have affected the measurement of the SNS tone indicator and skewed the value SNS tone indicator. For example, if the SNS tone indicator includes HRV, atrial fibrillation can cause an inaccurate HRV measurement for a certain period (e.g., one day out of the total monitoring period) since heart rate is not influenced by sympathetic tone during AT or AF. The user can then remove this skewed data from the monitoring period to determine a more accurate value of the patient's HRV. In various embodiments, the processor that analyzes the cardiac data can include algorithms that remove any apparent irregular data points to automatically correct for the anomalies.

Using the SNS indicator(s), the method 400 can continue by assessing whether the patient's SNS tone is elevated based on the SNS tone indicator(s) (decision block 425). The determination of whether the patient's SNS tone is high or elevated can be made by comparing the SNS tone indicator with a baseline or threshold value for that indicator. For example, if the SNS tone indicator is HRV, a low IRV value below a predetermined threshold value would indicate as an elevated SNS tone. Similarly, if the patient has a low DND, meaning that the patient's nighttime heart rate does not differ significantly from the patient's daytime heart rate, the patient may have elevated SNS tone. The predetermined threshold may be an absolute value (e.g., related to known data of healthy HRV or DND), or may be patient-specific. The comparison of the SNS tone indicator(s) to a threshold value and/or other assessment of the SNS indicators can be performed by a clinician or automatically using algorithms run by a processor. As shown in FIG. 4, if the SNS tone indicator is indicative of elevated SNS tone, then the patient is expected to be receptive to autonomic modulation therapy and the method 400 can continue to block 430 to perform autonomic modulation therapy. The autonomic modulation therapy may include renal nerve denervation therapy, baroreceptor activation therapy, carotid body modulation, mechanical carotid baroreceptor stimulation, intrathecal clonidine infusion, vagal nerve stimulation, and/or other device-based treatments that modulate SNS tone to treat hypertension.

When the SNS tone indicators do not suggest that the SNS tone is elevated, this may indicate that the patient would not be receptive to renal neuromodulation or other autonomic modulation therapies and, therefore, would not be a good candidate for autonomic modulation therapy. Accordingly, the method 400 can continue to block 435 to determine if there are other potential hypertension treatments that would be better suited for patients without elevated SNS tone, such as particular pharmacological treatments, excepting those aimed at modulating the SNS (e.g., such as clonidine).

Figure 5:
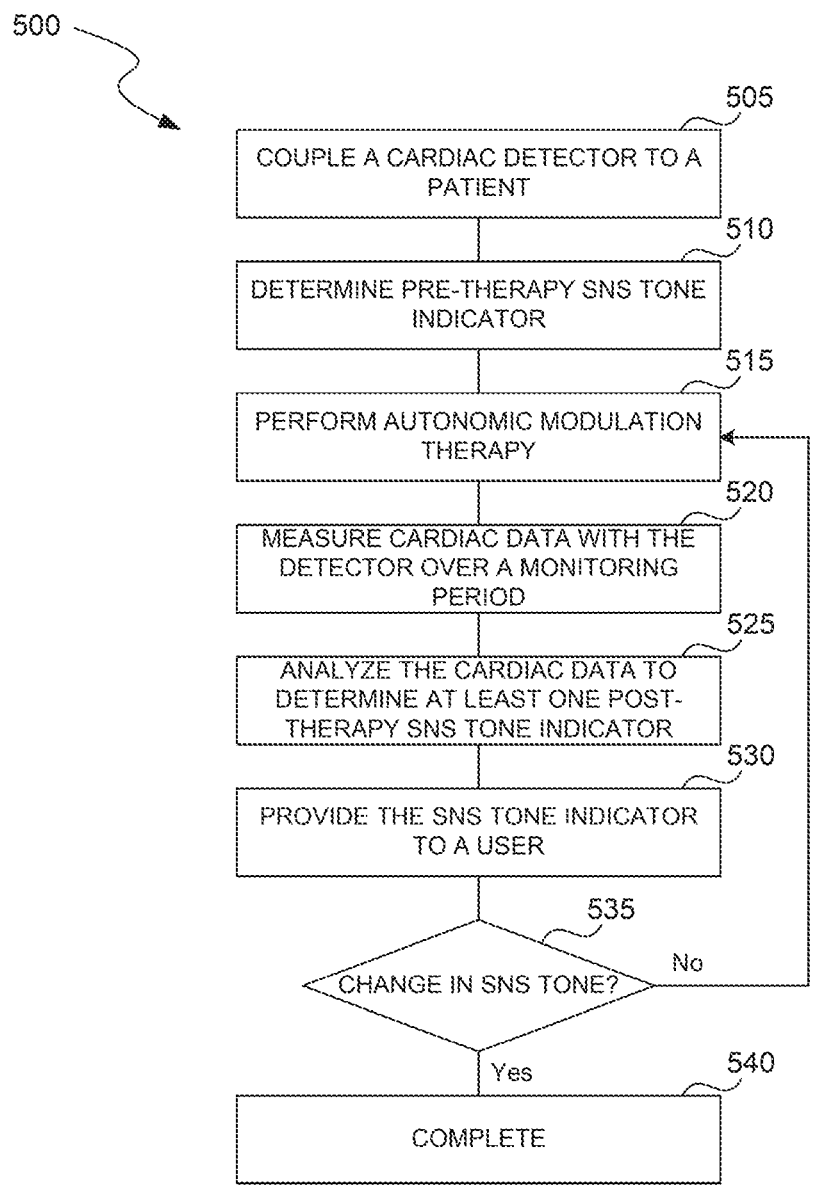
FIG. 5 is a block diagram illustrating a method of assessing SNS tone after autonomic modulation therapy in accordance with an embodiment of the present technology.

FIG. 5 is a block diagram illustrating a method 500 of assessing SNS tone after autonomic modulation therapy in accordance with an embodiment of the present technology. The method 500 can be implemented using the monitoring systems 100 and 300 described above with reference to FIGS. 1-3B, the neuromodulation system 600 described below with reference to FIGS. 7-8, and/or other suitable monitoring and neuromodulation systems. As shown in FIG. 5, the method 500 begins by implanting, attaching, or otherwise coupling a detector in or to a patient to record cardiac data (block 505), and determining a pre-therapy SNS tone indicator (block 510). The SNS tone indicator can be determined using the method 400 of FIG. 4 and/or other suitable methods for determining an SNS tone indicator. As discussed above, the SNS tone indicator can include HRV, night heart rate, DND, impedance variability, AT-AF burden, and/or combinations thereof. In various embodiments, additional physiological parameters, such as blood pressure or patient activity, can also be used in conjunction with the SNS tone indicators to provide an integrated diagnostic parameter indicative of a patient's SNS tone.

As shown in FIG. 5, the method 500 can further include performing an autonomic modulation therapy to treat hypertension (block 515). The autonomic modulation therapy can include renal neuromodulation, baroreceptor activation therapy, carotid body modulation, mechanical carotid baroreceptor stimulation, intrathecal clonidine infusion, vagal nerve stimulation, and/or other device-based treatments that modulate SNS tone to treat hypertension. Once the therapy is complete, the detector can be used to measure cardiac data over a monitoring period (block 520). For example, the detector can detect ECG data over a period of time (e.g., 10 days, 30 days, etc.). The detected data can be stored locally on the detector or transmitted (e.g., via a Bluetooth, cellular, or intranet connection) to a receiver external to the patient. The receiver may store the received data for further processing and/or may transmit the data to another remote device (e.g., a central computer). The monitoring period for recording the cardiac data may extend over several days, a week after modulation therapy, thirty days after therapy, three months post-therapy, six months post-therapy, intervals therebetween, and/or longer time periods post-therapy.

After the monitoring period, diagnostics can be run on the cardiac data to determine one or more post-therapy SNS tone indicators (block 525), and the SNS tone indicators are then provided to a user (e.g., a clinician) (block 530). The post-therapy SNS tone indicators can include HRV, night heart rate, DND, impedance variability, AT-AF burden (e.g., an arrhythmia indicator), patient activity level (e.g., a post-therapy activity indicator), other physiological parameters, and/or combinations thereof. The method 500 continues by comparing the pre- and post-therapy SNS tone indicators to determine if there has been a change in the SNS tone and, optionally, to what degree the SNS tone indicators have changed (decision block 535). For example, when the SNS tone indicator is HRV, an increase in HRV and/or DND from pre-therapy to post-therapy may indicate that the autonomic modulation therapy had a positive therapeutic effect on the patient that will result in a decrease in blood pressure. A decrease in post-therapy night heart rate compared to pre-therapy night heart rate can indicate a positive therapeutic effect of the therapy. An increase from the pre-therapy patient activity level indicator to the post-therapy patient activity level could a positive therapeutic effect. If there has been a change in the SNS tone indicator value before and after therapy and/or if the post-therapy SNS indicator value has changed to a desired degree, the autonomic modulation therapy may be considered successful, and the method 500 may be deemed complete (block 540).

If the comparison between the pre- and post-therapy SNS tone indicators shows that there has not been a change between the pre- and post-therapy SNS tone indicators, or if the post-therapy SNS tone indicator is still indicative of an elevated SNS tone, this may be a sign that the therapy did not provide the desired therapeutic effect and that further therapy may be necessary or that the patient was not a good candidate for the therapy from the outset. In this case, the method 500 may, optionally, continue by repeating the autonomic modulation therapy (block 515) to further treat the hypertension. For example, when the therapy is renal neuromodulation, the method 500 can continue by further ablating or modulating the renal nerves and then again determining whether there has been a change in the post-therapy SNS tone indicator. These steps (blocks 515-535) can be repeated until the desired change in SNS tone indicator is achieved. In various embodiments, block 535 of the method 500 can include comparing the post-therapy SNS tone indicator to a standardized SNS tone indicator value that corresponds to a normal or healthy SNS tone. For example, if the selected SNS tone indicator is HRV, the post-therapy HRV value can be compared to a standardized "normal" HRV range. If the post-therapy HRV value is outside of the normal HRV range, the method 500 can continue by repeating the therapy and again measuring the SNS tone indicator to determine whether it is within the normal range.

The method 500 can be used by clinicians to determine if an autonomic modulation therapy has been effective to treat hypertension. For example, certain therapies may successfully modulate the SNS, but the therapeutic effects on the patient's blood pressure may not be detectable for an extended period of time post-therapy (e.g., 1 month, 3 months, 6 months, 1 year). However, the therapeutic effect on the SNS tone may be detectable before the change in blood pressure and, therefore, the method 500 may be used to confirm that a therapy has been effective before a noticeable blood pressure change has occurred. This also avoids the circumstance where a patient is subject to multiple autonomic modulation therapies because them has not been a change in blood pressure, but the desired modulation has already been achieved. Accordingly, the method 500 may be used as an indicator that an autonomic modulation therapy has the desired therapeutic effect.

Figure 6:
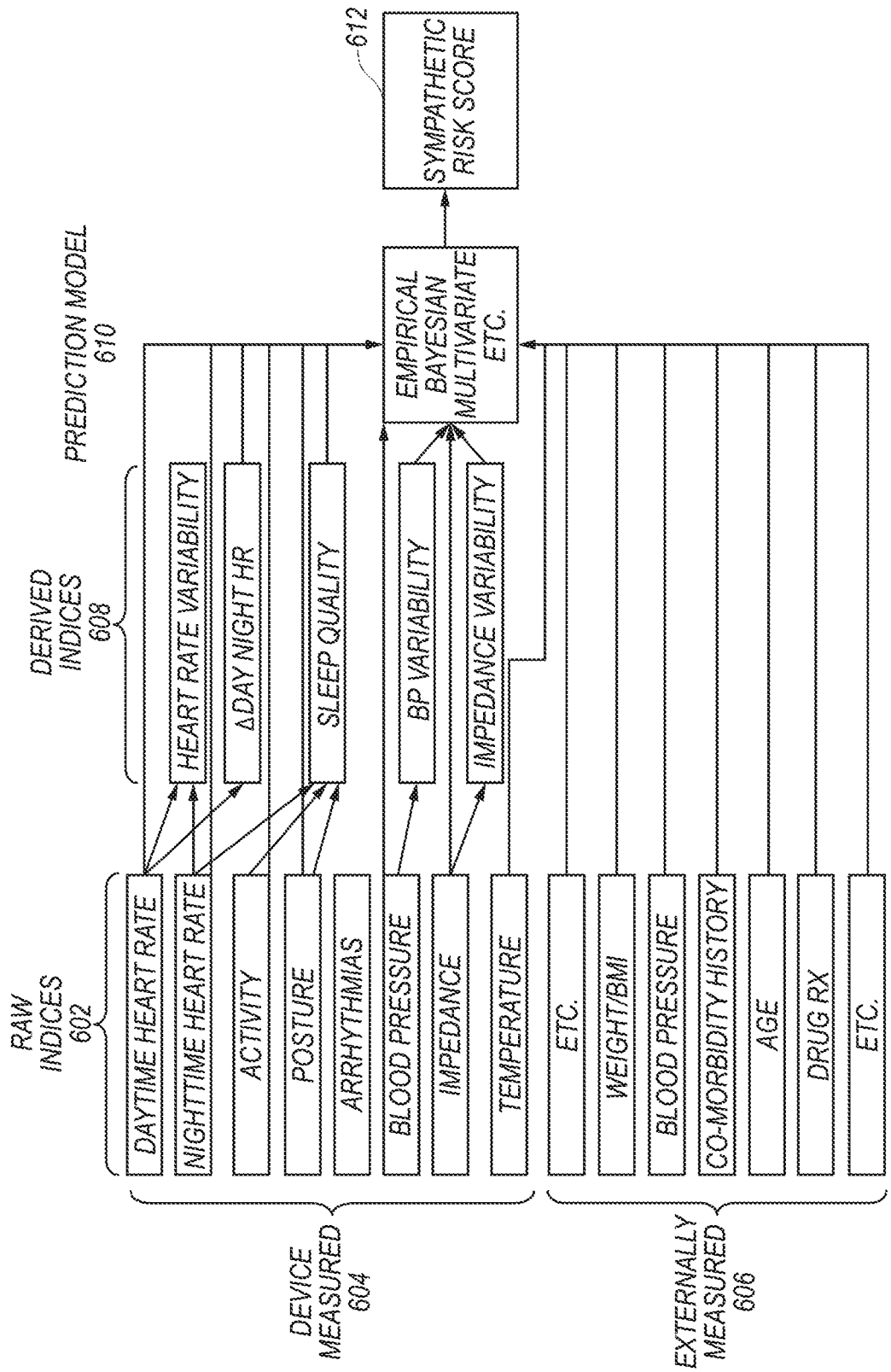
FIG. 6 is a block diagram illustrating a method for determining sympathetic tone score in accordance with an embodiment of the present technology.

FIG. 6 is a block diagram illustrating a method 600 for determining sympathetic tone score in accordance with an embodiment of the present technology. The method 600 is performed automatically by a computing device or system, such as those described below with reference to FIGS. 9 and 10, and can be used to determine sympathetic tone scores for the methods 400 and 500 described above with reference to FIGS. 4 and 5. As shown in FIG. 6, the method 600 can include capturing one or more raw indices 602 that may be indicative of sympathetic tone and responsiveness to neuromodulation therapy. Certain indices (identified as "device-measured indices 604") may be measured using a monitoring device, such as the monitoring systems 100, 300 described with reference to FIGS. 1-3B or other suitable monitoring systems. The device-measured indices 604 can include, for example, daytime heart rate, nighttime heart rate, activity, posture, arrhythmias, blood pressure, impedance, temperature, and/or other suitable indices that can be detected via an implanted or external cardiac device or other monitoring device. These indices 604 can be measured over a period of time, such as several hours, 24 hours, numerous days, one or more weeks, one or mom months, and/or other suitable time periods. This information can be sent from the monitoring device to the computing system via a wireless or wired connection. The method 600 can also take into account other, externally-measured indices 606 using other detection devices and/or patient information, and this information can be entered or otherwise transmitted to the computing system. For example, the externally-measured indices 606 that can be taken into account may include body weight and/or BMI, blood pressure, co-morbidity history, age, drug prescription history, race, and/or other indices indicative of sympathetic tone and responsiveness to neuromodulation therapy.

As shown in FIG. 6, the method 600 can process certain information from the device-measured indices 604 to provide one or more derived indices 608. For example, daytime and nighttime heart rate can be used to determine heart rate variability and/or the difference between day and night heart rate; daytime heart rate, nighttime heart rate, activity, and posture can be used to determine sleep quality; blood pressure can be used to determine blood pressure variability; and/or impedance can be used to determine impedance variability. In other embodiments, the method 600 can derive additional indices that may be indicative of sympathetic tone. In further embodiments, the method 600 may derive some of the indices 608 using externally-measured indices 606.

The raw indices 602 and the derived indices 608 can then be analyzed via one or more predictive models that are indicative of sympathetic tone. For example, the indices 602, 608 can be analyzed using empirical models, Bayesian models, multivariate models, and/or other predictive models that result in an integrated SNS tone or sympathetic risk score 612. In certain embodiments, the indices can be weighted depending on their relationship to sympathetic nerve tone. For example, indices that are closely tied to high sympathetic nerve tone may be weighted heavier than indices that are less closely related to SNS tone.

The integrated sympathetic risk score 612 can be indicative of whether a particular patient having high sympathetic tone would make a good candidate for a specific therapy that affects SNS tone, such as renal neuromodulation therapy. That is, the method 600 can predict whether therapy will be effective for such a patient given various indices tied to SNS tone. Similar to the method 400 of FIG. 4, if the integrated sympathetic risk score 612 is above a threshold valve or range, the method 600 can indicate to a clinician, the patient, and/or other user of the system that the patient would benefit from the specific therapy. In contrast, if the integrated sympathetic risk score 612 is lower than the threshold value or range, the method 600 can indicate to the user that the patient would not be a good candidate for the therapy. In further embodiments, a patient's sympathetic risk score 612, as determined via the method 600, can be compared before and after an SNS tone therapy to determine whether the therapy was effective (e.g., similar to the method 500 of FIG. 5). The sympathetic risk score 612 and, optionally, the various indices considered in the sympathetic risk score 612 can be provided to the user via a user interface, such as on a tablet computer, a smart phone, a computer, and/or another type of computing device.

II. SELECTED EMBODIMENTS OF NEUROMODULATION SYSTEMS

Figure 7:
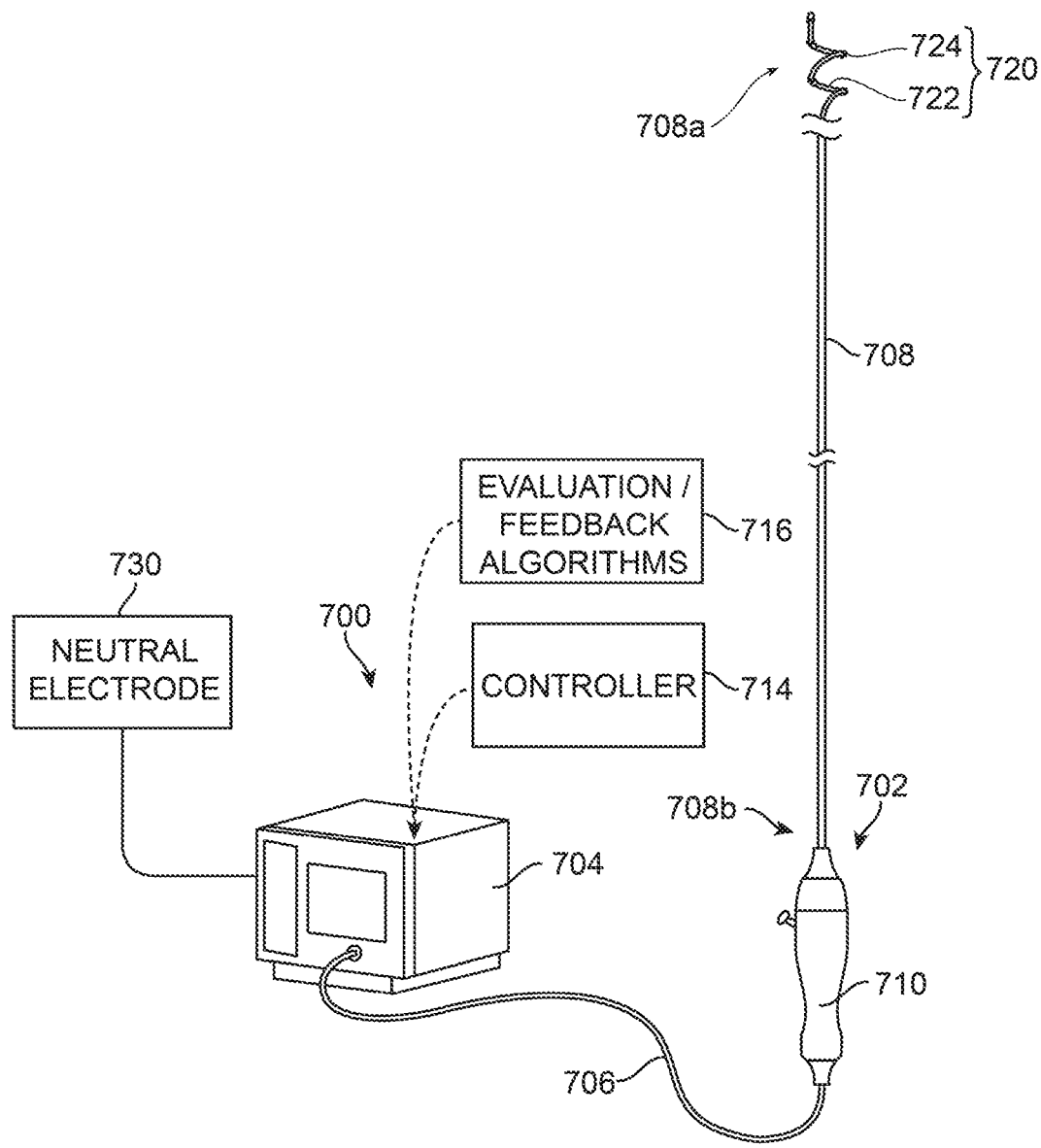
FIG. 7 is a partially schematic illustration of a neuromodulation system configured in accordance with another embodiment of the present technology.

FIG. 7 is a partially schematic illustration of a therapeutic neuromodulation system 700 ("system 700") configured in accordance with an embodiment of the present technology. The system 700 can be used in conjunction with the monitoring systems 100 and 300 described above with references to FIGS. 1-3 to evaluate a patients SNS tone before and/or after neuromodulation therapy. In addition, the system 700 can be used to provide the autonomic modulation therapy of the methods described in FIGS. 4 and 5.

As shown in FIG. 7, the system 700 includes a neuromodulation catheter 702, a console 704, and a cable 706 extending therebetween. The neuromodulation catheter 702 can include an elongated shaft 708 having a proximal portion 708b, a distal portion 708a, a handle 710 operably connected to the shaft 708 at the proximal portion 708b, and a neuromodulation assembly 720 operably connected to the shaft 708 at the distal portion 708a. The shaft 708 and the neuromodulation assembly 720 can be 2, 3, 4, 5, 6, or 7 French or another suitable size. As shown in FIG. 7, the neuromodulation assembly 720 can include a support structure 722 carrying an array of two or more electrodes 724. The electrodes 724 can be configured to apply electrical stimuli (e.g., RF energy) to target sites at or proximate to vessels within a patient, temporarily stun nerves, deliver neuromodulation energy to target sites, and/or detect vessel impedance. In various embodiments, certain electrodes 724 can be dedicated to applying stimuli, and the neuromodulation assembly 720 can include other types of therapeutic elements that provide neuromodulation therapy using various modalities, such cryotherapeutic cooling, ultrasound energy, etc.

The distal portion 708a of the shaft 708 is configured to be moved within a lumen of a human patient and locate the neuromodulation assembly 720 at a target site within or otherwise proximate to the lumen. For example, shaft 708 can be configured to position the neuromodulation assembly 720 within a blood vessel, a duct, an airway, or another naturally occurring lumen within the human body. In certain embodiments, intravascular delivery of the neuromodulation assembly 720 includes percutaneously inserting a guide wire (not shown) into a body lumen of a patient and moving the shaft 708 and/or the neuromodulation assembly 720 along the guide wire until the neuromodulation assembly 720 reaches a target site (e.g., a renal artery). For example, the distal end of the neuromodulation assembly 720 may define a passageway for engaging the guide wire for delivery of the neuromodulation assembly 720 using over-the-wire (OTW) or rapid exchange (RX) techniques. In other embodiments, the neuromodulation catheter 702 can be a steerable or non-steerable device configured for use without a guide wire. In still other embodiments, the neuromodulation catheter 702 can be configured for delivery via a guide catheter or sheath (not shown). Once at the target site, the neuromodulation assembly 720 can be configured to provide or facilitate neuromodulation therapy at the target site (e.g., using the electrodes 724 and/or other energy delivery elements).

The console 704 can be configured to control, monitor, supply, and/or otherwise support operation of the neuromodulation catheter 702. The console 704 can further be configured to generate a selected form and/or magnitude of energy for delivery to tissue at the target site via the neuromodulation assembly 720, and therefore the console 704 may have different configurations depending on the treatment modality of the neuromodulation catheter 702. For example, when the neuromodulation catheter 702 is configured for electrode-based, heat-element-based, or transducer-based treatment, the console 704 can include an energy generator (not shown) configured to generate RF energy (e.g., monopolar and/or bipolar RF energy), pulsed electrical energy, microwave energy, optical energy, ultrasound energy (e.g., intravascularly delivered ultrasound, extracorporeal ultrasound, and/or HIFU), direct heat energy, radiation (e.g., infrared, visible, and/or gamma radiation), and/or another suitable type of energy. When the neuromodulation catheter 702 is configured for cryotherapeutic treatment, the console 704 can include a refrigerant reservoir (not shown), and can be configured to supply the neuromodulation catheter 702 with refrigerant. Similarly, when the neuromodulation catheter 702 is configured for chemical-based treatment (e.g., drug infusion), the console 704 can include a chemical reservoir (not shown) and can be configured to supply the neuromodulation catheter 702 with one or more chemicals.

In selected embodiments, the system 700 may be configured to deliver a monopolar electric field via one or more of the electrodes 724. In such embodiments, a neutral or dispersive electrode 730 may be electrically connected to the console 704 and attached to the exterior of the patient. In embodiments including multiple electrodes 724, the electrodes 724 may deliver power independently (i.e., may be used in a monopolar fashion), either simultaneously, selectively, or sequentially, and/or may deliver power between any desired combination of the electrodes 724 (i.e., may be used in a bipolar fashion). In addition, an operator optionally may be permitted to choose which electrodes 724 are used for power delivery in order to form highly customized lesion(s) within the renal artery, as desired. One or more sensors (not shown), such as one or more temperature (e.g., thermocouple, thermistor, etc.), pressure, optical, flow, chemical, and/or other sensors, may be located proximate to, within, or integral with the electrodes 724. The sensor(s) and the electrodes 724 can be connected to one or more supply wires (not shown) that transmit signals from the sensor(s) and/or convey energy to the electrodes 724.

In various embodiments, the system 700 can further include a controller 714 communicatively coupled to the neuromodulation catheter 702. The controller 714 can be configured to initiate, terminate, and/or adjust operation of one or more components (e.g., the electrodes 724) of the neuromodulation catheter 702 directly and/or via the console 704. In other embodiments, the controller 714 can be omitted or have other suitable locations (e.g., within the handle 710, along the cable 706, etc.). The controller 714 can be configured to execute an automated control algorithm and/or to receive control instructions from an operator. Further, the console 704 can be configured to provide feedback to an operator before, during, and/or after a treatment procedure via an evaluation/feedback algorithm 716. In various embodiments, the controller 714 can be communicatively connected to the monitoring systems 100, 300 of FIGS. 1 and 3A-3B, and run diagnostics on the data recorded by the detectors 102, 304 to determine SNS tone indicators.

Figure 8:
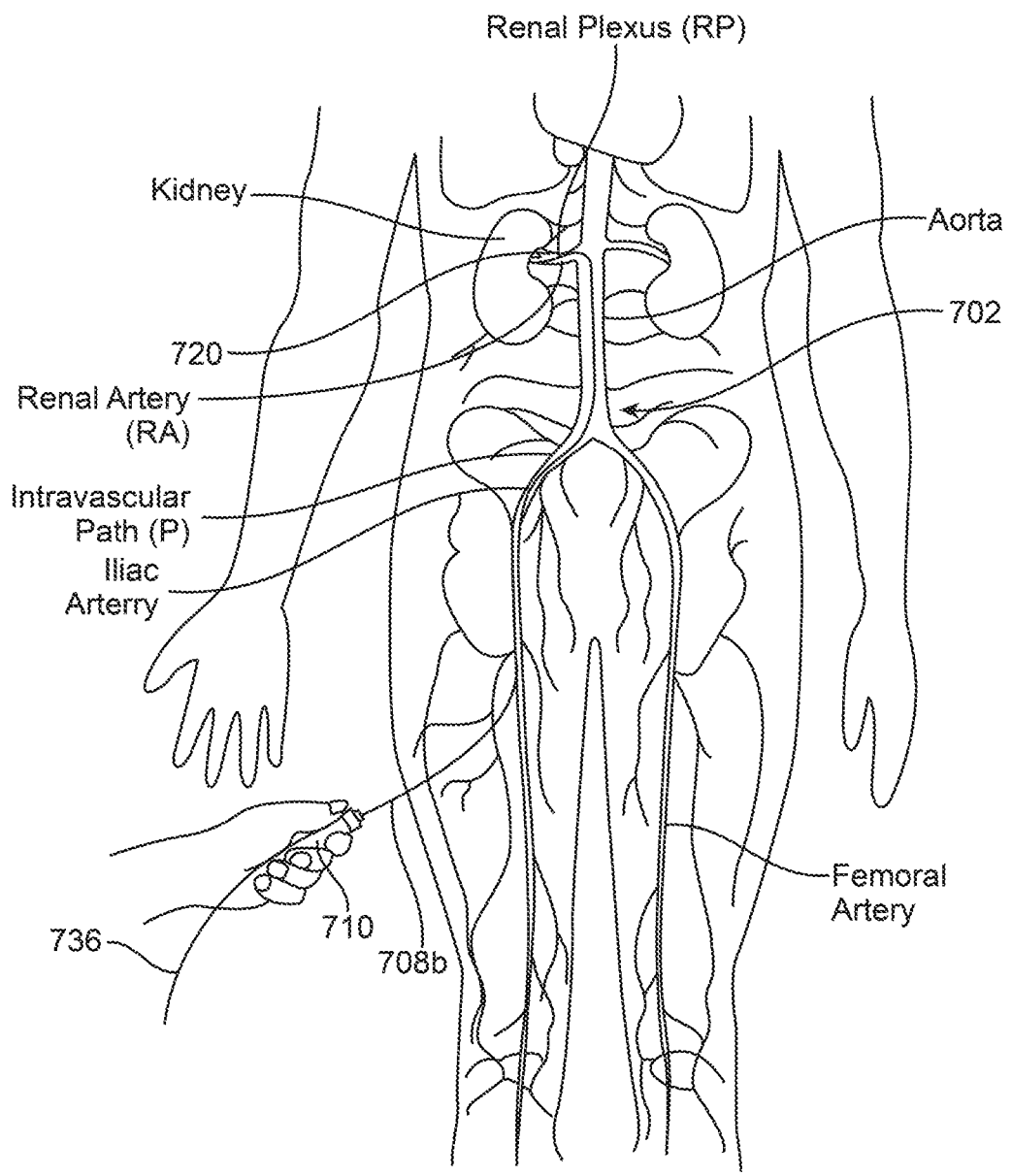
FIG. 8 illustrates modulating renal nerves and/or evaluating the neuromodulation therapy with the system of FIG. 7 in accordance with an embodiment of the present technology.

FIG. 8 (with additional reference to FIG. 7) illustrates modulating renal nerves in accordance with an embodiment of the system 700. The neuromodulation catheter 702 provides access to the renal plexus RP through an intravascular path P, such as a percutaneous access site in the femoral (illustrated), brachial, radial, or axillary artery to a targeted treatment site within a respective renal artery RA. By manipulating the proximal portion 708b of the shaft 708 from outside the intravascular path P, a clinician may advance the shaft 708 through the sometimes tortuous intravascular path P and remotely manipulate the distal portion 708a (FIG. 7) of the shaft 708. In the embodiment illustrated in FIG. 8, the neuromodulation assembly 720 is delivered intravascularly to the treatment site using a guide wire 736 in an OTW technique. As noted previously, the distal end of the neuromodulation assembly 720 may define a passageway for receiving the guide wire 736 for delivery of the neuromodulation catheter 702 using either OTW or RX techniques. At the treatment site, the guide wire 736 can be at least partially withdrawn or removed, and the neuromodulation assembly 720 can transform or otherwise be moved to a deployed arrangement for delivering energy at the treatment site. In other embodiments, the neuromodulation assembly 720 may be delivered to the treatment site within a guide sheath (not shown) with or without using the guide wire 736. When the neuromodulation assembly 720 is at the target site, the guide sheath may be at least partially withdrawn or retracted and the neuromodulation assembly 720 can be transformed into the deployed arrangement. In still other embodiments, the shaft 708 may be steerable itself such that the neuromodulation assembly 720 may be delivered to the treatment site without the aid of the guide wire 736 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 720. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 720. Further, in some embodiments, image guidance components (e.g., IVUS, OCT) may be integrated with the neuromodulation catheter 702 and/or run in parallel with the neuromodulation catheter 702 to provide image guidance during positioning of the neuromodulation assembly 720. For example, image guidance components (e.g., IVUS or OCT) can be coupled to the neuromodulation assembly 720 to provide three-dimensional images of the vasculature proximate the target site to facilitate positioning or deploying the multi-electrode assembly within the target renal blood vessel.

Energy from the electrodes 724 (FIG. 7) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Figure 9:
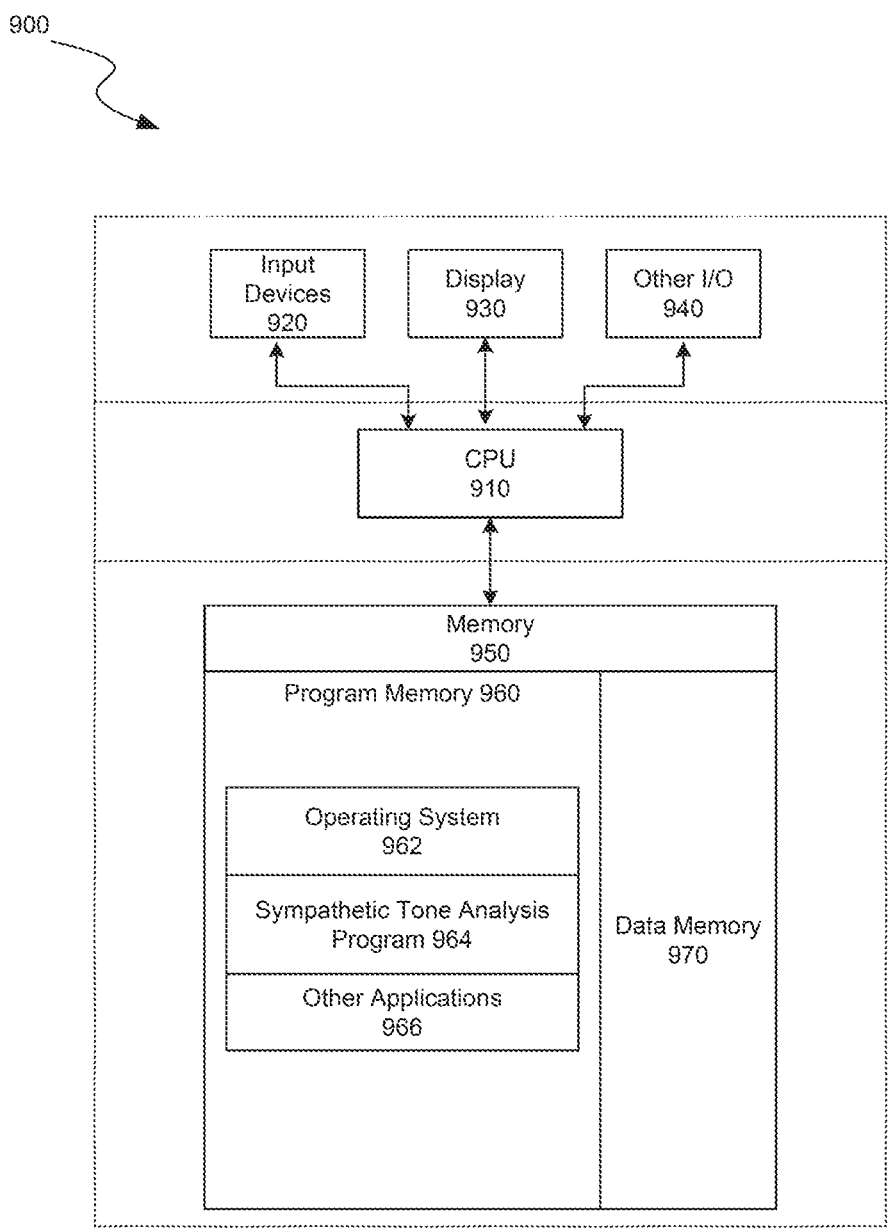
FIG. 9 is a block diagram illustrating an overview of devices on which some implementations of the present technology may operate.

FIG. 9 is a block diagram illustrating an overview of devices on which some implementations of the disclosed technology can operate. The devices can comprise hardware components of a device 900 for analyzing a user or patient's SNS tone and providing a sympathetic risk score. Device 900 can include, for example, one or more input devices 920 providing input to a central processing unit ("CPU"; processor) 910, notifying the CPU 910 of actions. The actions are typically mediated by a hardware controller that interprets the signals received from the input device and communicates the information to the CPU 910 using a communication protocol. The input devices 920 include, for example, a receiver for receiving signals from a monitoring device (e.g., the detectors 102, 302 described with reference to FIGS. 1-3B), a mouse, a keyboard, a touchscreen, an infrared sensor, a touchpad, a wearable input device, a camera- or image-based input device, a microphone, and/or other user input devices.

The CPU 910 can be a single processing unit or multiple processing units in a device or distributed across multiple devices. CPU 910 can be coupled to other hardware devices, for example, with the use of a bus, such as a PCI bus or SCSI bus. The CPU 910 can communicate with a hardware controller for devices, such as for a display 930. The display 930 can be used to display text and graphics. In some examples, the display 930 provides graphical and textual visual feedback to a user, such as a patient's sympathetic risk score, a summary of indices detected by a detector coupled to the device 900, and/or other suitable information. In some implementations, the display 930 includes the input device as part of the display, such as when the input device is a touchscreen or is equipped with an eye direction monitoring system. In some implementations, the display 930 is separate from the input device 920. Examples of display devices are: an LCD display screen, an LED display screen, a projected, holographic, or augmented reality display (such as a heads-up display device or a head-mounted device), and so on. Other I/O devices 940 can also be coupled to the processor, such as a network card, video card, audio card, USB, FireWire or other external device, camera, printer, speakers, CD-ROM drive, DVD drive, disk drive, or Blu-Ray device.

In some implementations, the device 900 also includes a communication device capable of communicating wirelessly or wire-based with a network node. The communication device can communicate with another device or a server through a network using, for example, TCP/IP protocols. Device 900 can utilize the communication device to distribute operations across multiple network devices.

The CPU 910 can have access to a memory 950. A memory includes one or more of various hardware devices for volatile and non-volatile storage, and can include both read-only and writable memory. For example, a memory 950 can include random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. The memory 950 can include program memory 960 for storing programs and software, such as an operating system 962, an SNS tone analysis program 964, and other application programs 966. The sympathetic tone analysis program 964, for example, can include one or more algorithms for analyzing various indices related to a patient's SNS tone (e.g., data received from a cardiac detector), providing a sympathetic tone summary or report, providing a sympathetic tone score, and/or providing a recommendation for a specific therapy (e.g., renal denervation). The memory 950 can also include data memory 970 including recorded data from a cardiac detector, patient data, algorithms related to sympathetic tone analysis, configuration data, settings, user options or preferences, etc., which can be provided to the program memory 960 or any element of the device 900.

Some implementations can be operational with numerous other general purpose or special purpose computing system environments or configurations. Examples of well-known computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, set-top boxes, programmable consumer electronics, network PCs, minicomputers, mainframe computers, distributed computing environments that include any of the above systems or devices, or the like.

Figure 10:
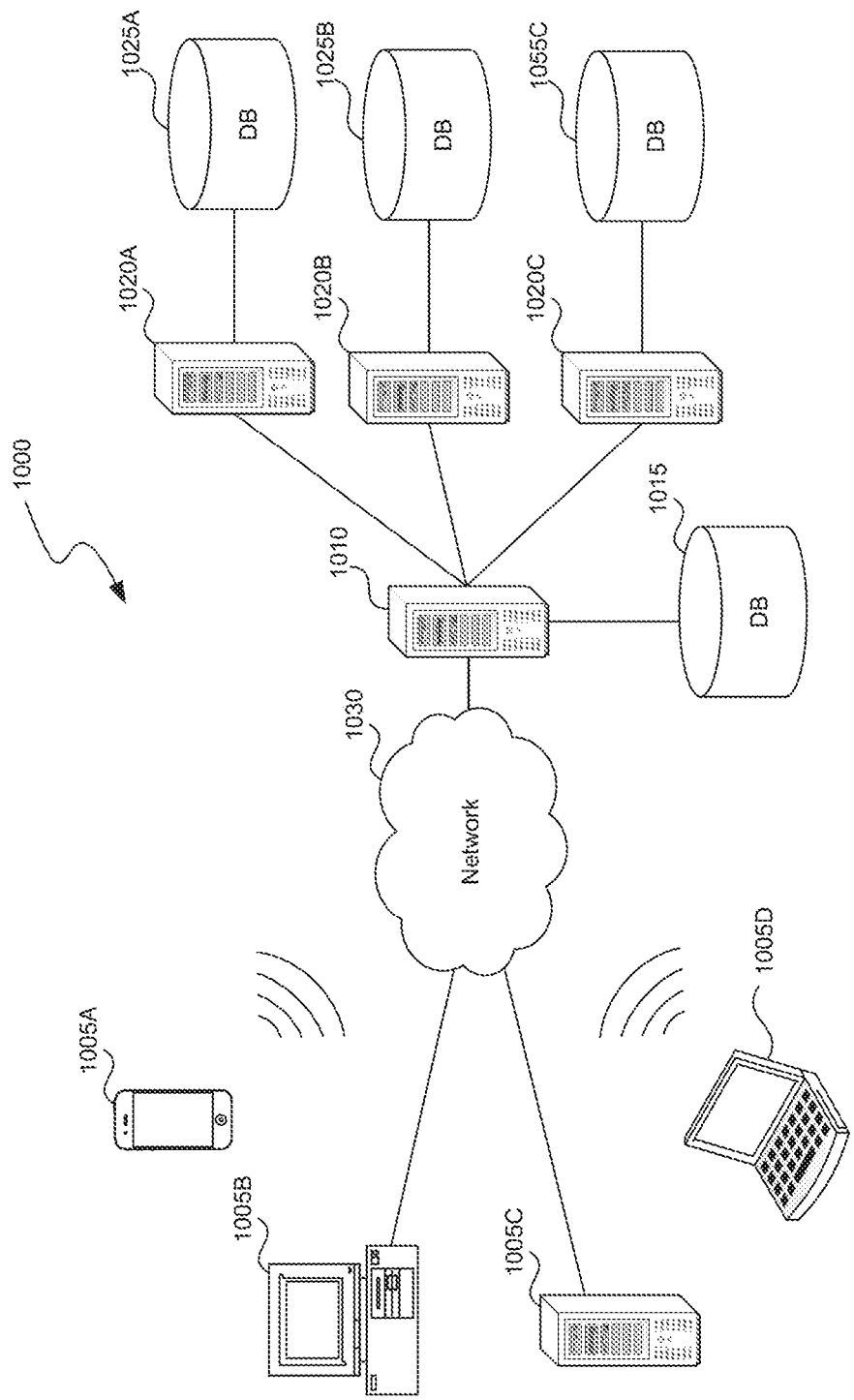
FIG. 10 is a block diagram illustrating an overview of an environment in which some implementations of the present technology may operate.

FIG. 10 is a block diagram illustrating an overview of an environment 1000 in which some implementations of the disclosed technology can operate. The environment 1000 can include one or more client computing devices 1005A-D (identified collectively as "client computing devices 1005"), examples of which can include the device 900 of FIG. 9. The client computing devices 1005 can operate in a networked environment using logical connections through a network 1030 to one or more remote computers, such as a server computing device 1010.

In some implementations, server 1010 can be an edge server that receives client requests and coordinates fulfillment of those requests through other servers, such as servers 1020A-C. The server computing devices 1010 and 1020 can comprise computing systems, such as device 900 (FIG. 9). Though each server computing device 1010 and 1020 is displayed logically as a single server, the server computing devices 1010 and 1020 can each be a distributed computing environment encompassing multiple computing devices located at the same or at geographically disparate physical locations. In some implementations, each server 1020 corresponds to a group of servers.

The client computing devices 1005 and the server computing devices 1010 and 1020 can each act as a server or client to other server/client devices. The server 1010 can connect to a database 1015. The servers 1020A-C can each connect to a corresponding databases 1025A-C. As discussed above, each server 1020 can correspond to a group of servers, and each of these servers can share a database or can have their own database. The databases 1015 and 1025 can warehouse (e.g. store) information such as raw indices related to patient sympathetic tone, other patient information, algorithms for deriving indices related of sympathetic tone, and/or other information necessary for the implementation of the systems and methods described above with respect to FIGS. 1-8. Though the databases 1015 and 1025 are displayed logically as single units, the databases 1015 and 1025 can each be a distributed computing environment encompassing multiple computing devices, can be located within their corresponding server, or can be located at the same or at geographically disparate physical locations.

The network 1030 can be a local area network (LAN) or a wide area network (WAN), but can also be other wired or wireless networks. The network 1030 may be the Internet or some other public or private network. The client computing devices 1005 can be connected to the network 1030 through a network interface, such as by wired or wireless communication. While the connections between the server 1010 and servers 1020 are shown as separate connections, these connections can be any kind of local, wide area, wired, or wireless network, including the network 1030 or a separate public or private network.

III. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

IV. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 11:
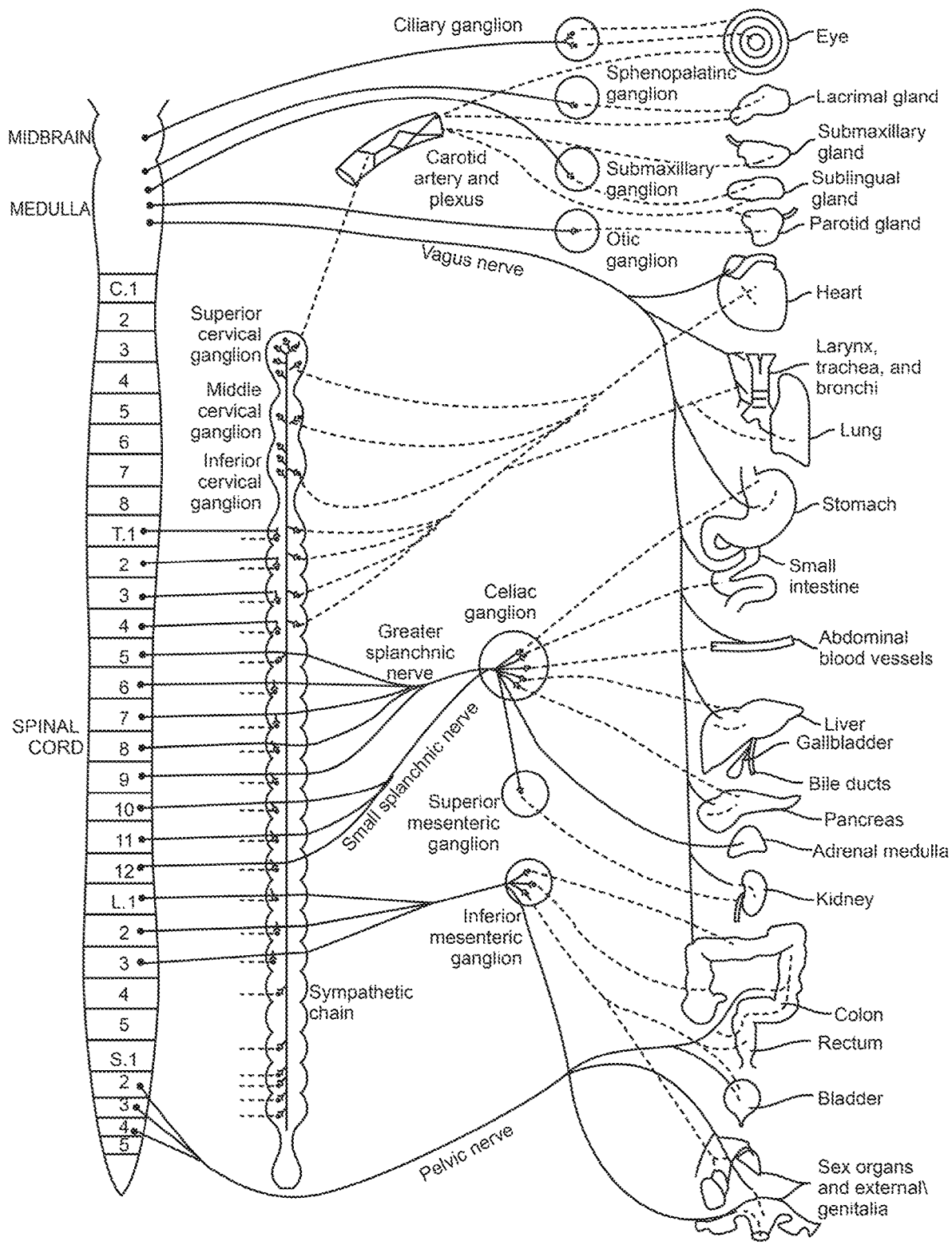
FIG. 11 is a conceptual illustration of the sympathetic nervous system (SNS) and how the brain communicates with the body via the SNS.

As shown in FIG. 11, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifuration) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 12:
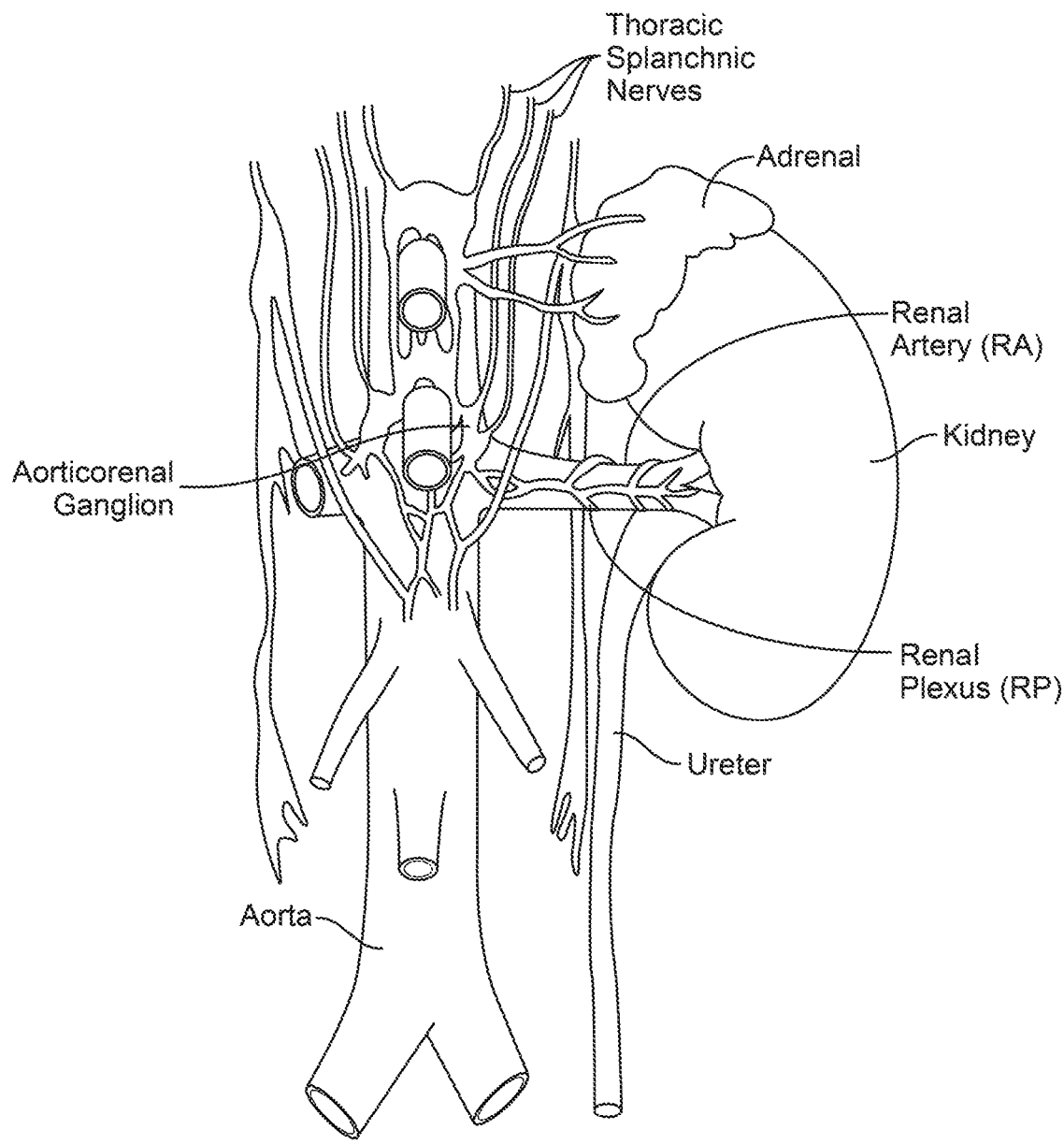
FIG. 12 is an enlarged anatomic view of nerves innervating a left kidney to form the renal plexus surrounding the left renal artery.

As FIG. 12 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 13:
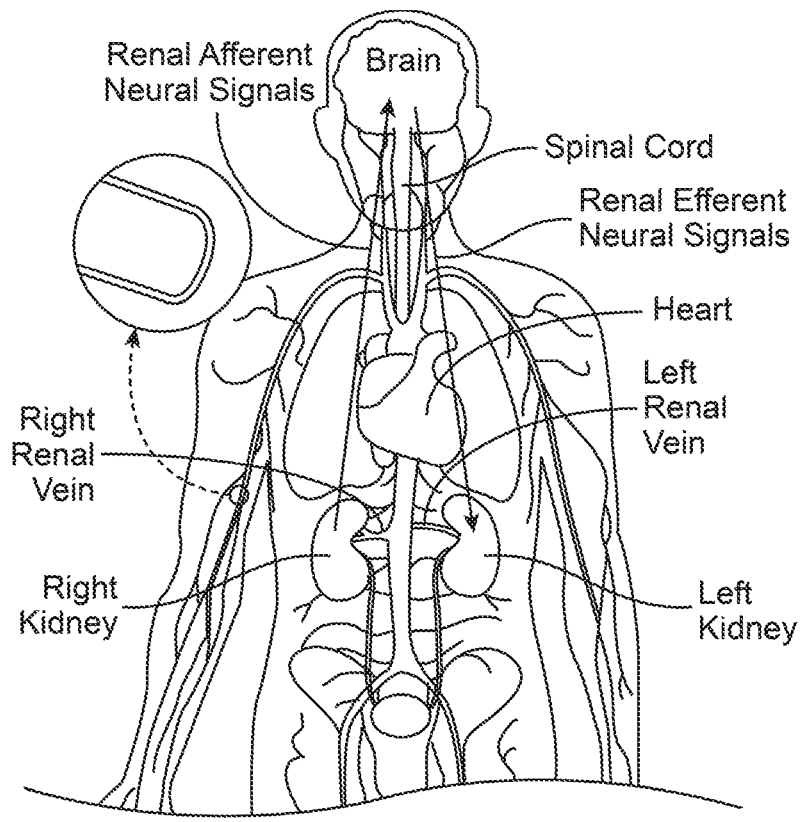
FIGS. 13 and 14 are anatomic and conceptual views, respectively, of a human body depicting neural efferent and afferent communication between the brain and kidneys.
Figure 14:
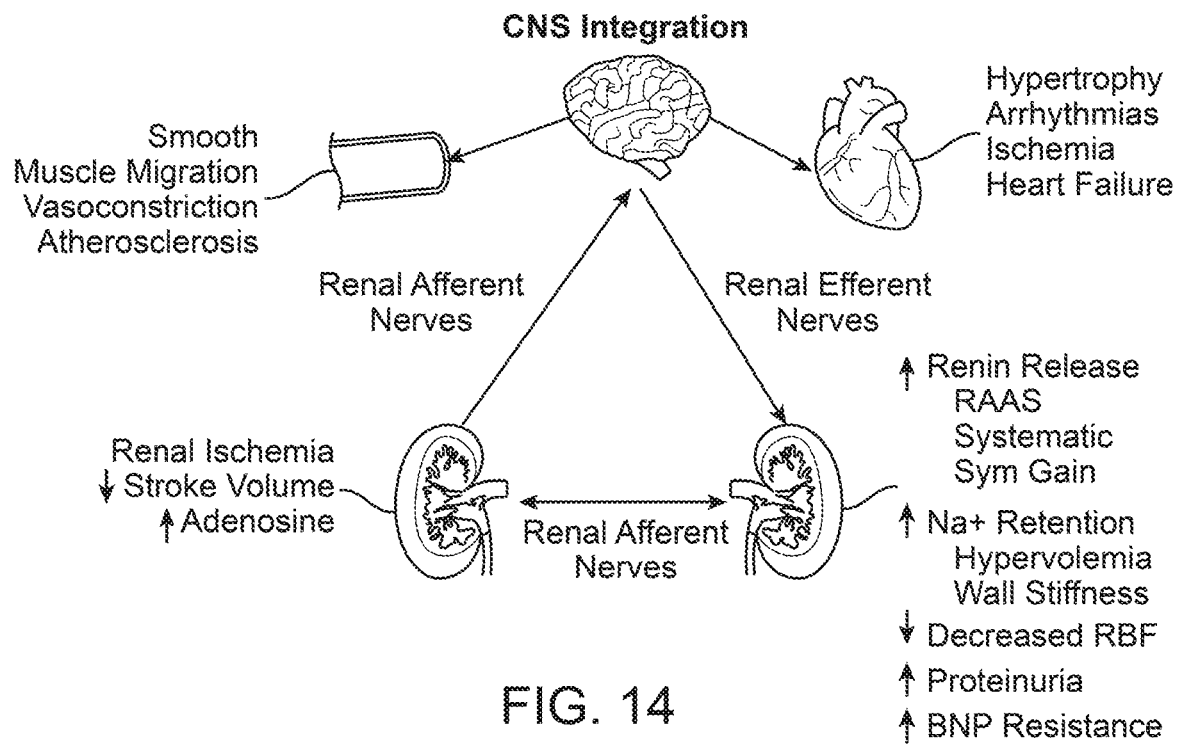

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 13 and 14, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 11. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 15:
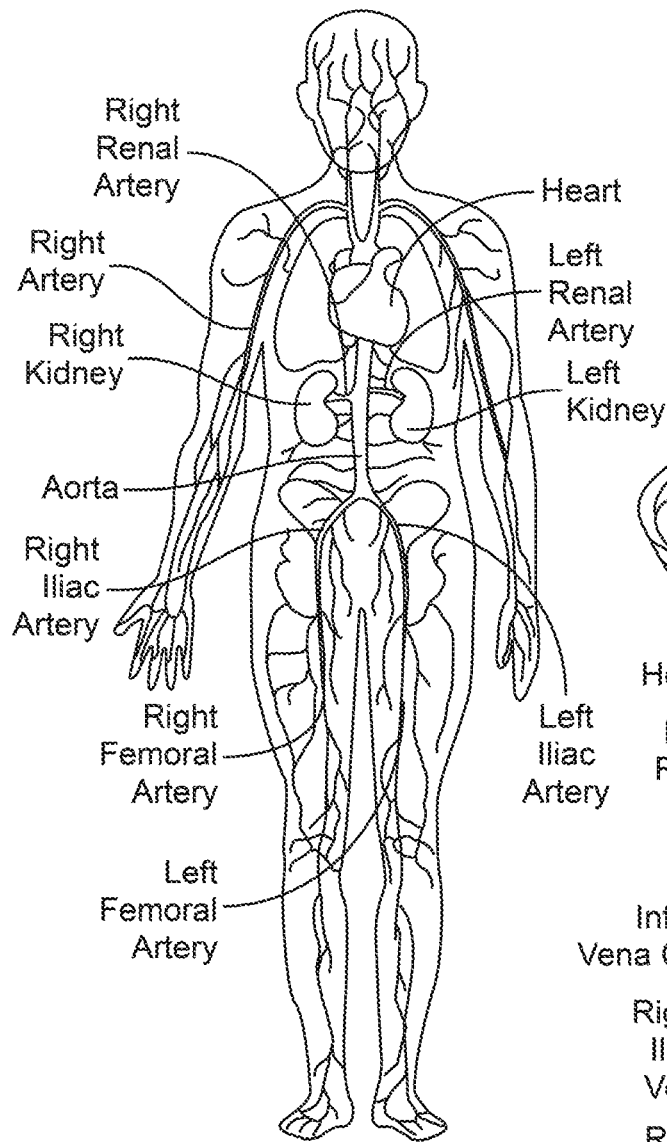
FIGS. 15 and 16 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 15 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 16:
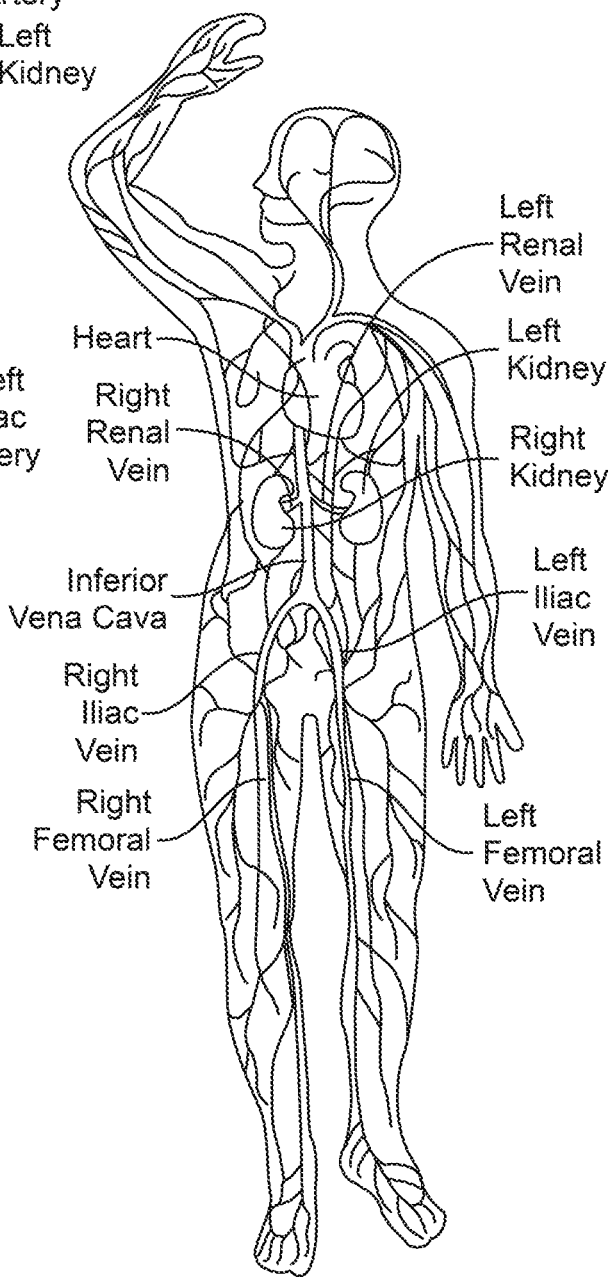

As FIG. 16 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

V. ADDITIONAL EXAMPLES

1. A method performed by a computing device for evaluating sympathetic nervous system (SNS) tone of a patient, the method comprising:
    receiving, at a processor, sensed data from a detector during a monitoring period, wherein the detector is coupled to the patient and configured to detect cardiac measurements of the patient related to SNS tone, wherein the cardiac measurements include heart rate, and wherein the processor is wirelessly coupled to the detector;
    determining, at the processor, derived indices indicative of SNS tone, wherein the derived indices are derived using at least some of the cardiac measurements received from the detector;
    determining, at the processor, an SNS risk score based on a plurality of indices including at least some of the cardiac measurements received from the detector and the derived indices;
    displaying, on a user interface coupled to the processor, the SNS risk score to a user;
    comparing, via the processor, the SNS risk score to a threshold SNS score indicative of elevated SNS tone suitable for renal neuromodulation therapy; and
    providing, via the user interface, a recommendation of whether to proceed with renal neuromodulation therapy based on the comparison between the SNS risk score and the threshold SNS score.
2. The method of example 1 wherein receiving the sensed data comprises receiving daytime heart rate, nighttime heart rate, blood pressure, posture, and activity level.
3. The method of example 2 wherein determining the plurality of derived indices comprises determining sleep quality based on nighttime heart rate, activity level, posture, and blood pressure.
4. The method of any one of examples 1-3 wherein receiving the sensed data comprises receiving activity level, posture, arrhythmia information, impedance, and blood pressure.
5. The method of any one of examples 1-4 wherein determining the plurality of derived indices comprises determining heart rate variability, day-night heart rate difference, impedance variability, atrial tachyarrhythmia-atrial fibrillation ("AT-AF") burden, sleep quality, and blood pressure variability.
6. The method of any one of examples 1-5, further comprising receiving, at the processor, a plurality of externally-measured indices separate from the sensed data, wherein the externally-measured indices comprise at least one of weight, body mass index, or age.
7. The method of any one of examples 1-6 wherein determining the SNS risk score comprises weighting the plurality of different indices differently based on association with SNS tone.
8. The method of any one of examples 1-7 wherein determining the SNS risk score based on the plurality of indices comprises determining the SNS score based on sensed data from the detector, the derived indices, and a plurality of externally-measured indices separate from the sensed data.
9. The method of any one of examples 1-8 wherein determining the SNS risk score comprises providing the SNS risk score based on an empirical predictive model.
10. The method of any one of examples 1-8 wherein determining the SNS risk score comprises providing the SNS risk score based on a Bayesian predictive model.
11. The method of any one of examples 1-8 wherein determining the SNS risk score comprises providing the SNS risk score based on a multivariate predictive model.
12. The method of any one of examples 1-11 wherein the monitoring period is at least 24 hours, and wherein the method further comprises:
    sensing data, via the detector, for at least 24 hours, wherein receiving the sensed data from the detector comprises receiving the sensed data throughout the monitoring period.
13. The method of any one of examples 1-12 wherein displaying the SNS risk score comprises displaying the SNS risk score on a tablet computer.
14. The method of any one of examples 1-13 wherein providing the recommendation of whether to proceed with renal neuromodulation therapy based on the SNS risk score comprises recommending renal neuromodulation therapy when the SNS risk score is above the threshold SNS score indicative of high SNS tone.
15. The method of any one of examples 1-14 wherein the SNS risk score is a first SNS risk score, and wherein the method further comprises:
    receiving, at the processor, sensed data from the detector after the patient has undergone renal neuromodulation therapy;
    determining, at the processor, a second SNS risk score based on a plurality of indices received or derived after renal neuromodulation therapy;
    displaying, on the user interface, the second SNS risk score to the user; and comparing, via the processor, the first SNS risk score to the second SNS risk score to determine whether renal neuromodulation therapy was effective for the patient.

16. A method of assessing sympathetic nervous system (SNS) tone of a human patient, the method comprising:
    measuring cardiac data with a detector for a monitoring period, wherein the detector is attached to and/or implanted in the human patient;
    analyzing the cardiac data to determine an SNS tone indicator, determining whether the SNS tone indicator is indicative of an elevated SNS tone of the human patient; and
    when the SNS tone is elevated, performing neuromodulation therapy on the human patient to treat hypertension.

17. A method of assessing sympathetic nervous system (SNS) tone of a human patient, the method comprising:
    determining a pre-therapy SNS tone indicator;
    applying neuromodulation therapy on the human patient to treat hypertension;
    determining a post-therapy SNS tone indicator;
    comparing the pre-therapy SNS tone indicator and the post-therapy SNS tone indicator to determine if there has been a change between the pre- and post-therapy SNS tone indicators;
    when there is no change between the pre- and post-therapy SNS tone indicators, applying neuromodulation therapy on the human patient to treat hypertension.

18. The method of example 17, further comprising determining a post-therapy activity indicator.

19. The method of example 18, further comprising determining a post-therapy arrhythmia detector.

20. A non-transitory computer readable memory storing instructions that, when executed by a processor of a computing device, cause the computing device to perform operations for evaluating sympathetic nervous system (SNS) tone of a human patient, the operations comprising:
    receiving sensed data from a detector during a monitoring period, wherein the detector is coupled to the patient and configured to detect cardiac measurements of the patient related to SNS tone, wherein the cardiac measurements include heart rate, and wherein the processor is wirelessly coupled to the detector;
    determining, via the processor, derived indices indicative of SNS tone, wherein the derived indices are derived using at least some of the cardiac measurements received from the detector;
    determining, via the processor, an SNS risk score based on a plurality of indices, wherein the plurality of indices include the derived indices;
    displaying, on a user interface, the SNS risk score to a user; comparing the SNS risk score to a threshold SNS score indicative of elevated SNS tone suitable for renal neuromodulation therapy; and
    providing, via the user interface, a recommendation of whether to proceed with renal neuromodulation therapy based on the comparison between the SNS risk score and the threshold SNS score.

21. A system for evaluating sympathetic nervous system (SNS) tone of a human patient, the system comprising:
    a detector configured to measure cardiac data and/or other detectable parameters of the patient, wherein the cardiac measurements include heart rate; and
    a receiver configured to receive the cardiac data detected by the detector and transmit the cardiac data to a computing device having a memory and a processor, wherein the memory stores instructions that, when executed by the processor, cause the system to perform operations comprising:
    determining, via the processor, derived indices indicative of SNS tone, wherein the derived indices are derived using at least some of the measured cardiac data received from the detector;
    determining, via the processor, an SNS risk score based on a plurality of indices, wherein the plurality of indices include the derived indices;
    displaying, on a user interface coupled to the processor, the SNS risk score to a clinician; comparing, via the processor, the SNS risk score to a threshold SNS score indicative of elevated SNS tone suitable for renal neuromodulation therapy; and
    providing, via the user interface, a recommendation of whether to proceed with renal neuromodulation therapy based on the comparison between the SNS risk score and the threshold SNS score.

VI. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical." and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A system comprising:
a memory; and
one or more processors configured to:
  determine a plurality of sympathetic nervous system (SNS) tone indicators based on cardiac data of a patient;
  determine that an abnormality is present within the plurality of SNS tone indicators;
  correct the abnormality within the plurality of SNS tone indicators;
  compare an SNS tone indicator of the plurality of SNS tone indicators to a stored value stored in the memory;
  determine that a neuromodulation therapy delivered to the patient was effective based on the comparison of the SNS tone indicator to the stored value.

2. The system of claim 1, wherein to correct the abnormality within the plurality of SNS tone indicators, the one or more processors are configured to:
  remove one or more irregular or skewed SNS tone indicators of the plurality of SNS tone indicators.

3. The system of claim 1, further comprising a detector configured to sense cardiac activity of the patient, wherein the one or more processors are configured to receive the cardiac data from with the detector.

4. The system of claim 1, further comprising a user interface in communication with the one or more processors, wherein the one or more processors are configured to display the plurality of SNS tone indicators via the user interface.

5. The system of claim 4, wherein the one or more processors are configured to provide, via the user interface, a recommendation to proceed with the neuromodulation therapy based on the comparison of the SNS tone indicator to the stored value.

6. The system of claim 1, wherein the plurality of SNS tone indicators comprises at least one of a heart rate variability (HRV), a night heart rate, an impedance variability, a net duration of atrial tachycardia (AT) or atrial fibrillation (AF), AT/AF burden, a patient activity level, or a day-night heart rate difference (DND).

7. The system of claim 1, wherein the one or more processors are configured to:
  control a medical device to deliver the neuromodulation therapy to the patient;
  determine a plurality of post-therapy SNS tone indicators based on cardiac data of the patient generated after delivery of the neuromodulation therapy to the patient;
  compare a post-therapy SNS tone indicator of the plurality of post-therapy SNS tone indicators to a respective pre-therapy SNS tone indicator of the plurality of pre-therapy SNS tone indicators; and
  determine that the neuromodulation therapy was effective on the patient based on a determination that the post-therapy SNS tone indicator differs from the respective pre-therapy SNS tone indicator.

8. The system of claim 7, wherein the one or more processors are configured to control the medical device to continue delivering the neuromodulation therapy to the patient based on a determination that the neuromodulation therapy was not effective.

9. The system of claim 7, wherein the one or more processors are configured to cause the medical device to terminate the delivery of the neuromodulation therapy to the patient based on a determination that the neuromodulation therapy was effective.

10. The system of claim 1, wherein the stored value comprises one or more of a baseline value or a threshold value for the SNS tone indicator of the plurality of SNS tone indicators.

11. A system comprising:
a memory;
a user interface; and
one or more processors configured to:
  determine a plurality of sympathetic nervous system (SNS) tone indicators based on cardiac data of a patient;
  determine a weight for each SNS tone indicator of the plurality of SNS tone indicators;
  determine an SNS risk score based on the two or more SNS tone indicators of the plurality of SNS tone indicators and the respective weights for each SNS tone indicator of the two or more SNS tone indicators;
  compare the SNS risk score to a stored SNS risk score stored in the memory, wherein the comparison indicates whether the patient is expected to be responsive to renal neuromodulation therapy; and
  provide, via the user interface and based on the comparison between the SNS risk score and the stored SNS risk score, a recommendation to deliver renal neuromodulation therapy to the patient.

12. The system of claim 11, wherein the one or more processors are configured to provide the recommendation to deliver the renal neuromodulation therapy based on a determination that the SNS risk score is greater than or equal to the stored SNS risk score.

13. The system of claim 11, wherein the plurality of SNS tone indicators comprises at least one of a heart rate variability (HRV), a night heart rate, an impedance variability, a net duration of atrial tachycardia (AT) or atrial fibrillation (AF), AT/AF burden, a patient activity level, or a day-night heart rate difference (DND).

14. The system of claim 11, wherein the one or more processors are configured to determine the SNS risk score based on the plurality of SNS tone indicators and a plurality of externally measured indices.

15. The system of claim 14, wherein the plurality of externally measured indices comprises one or more of a weight of the patient, a body mass index of the patient, or an age of the patient.

16. A method of evaluating effectiveness of neuromodulation therapy on a patient, the method comprising:
- determining, by one or more processors, a plurality of sympathetic nervous system (SNS) tone indicators based on cardiac data of the patient;
- determining, by the one or more processors, a weight for each SNS tone indicator of the plurality of SNS tone indicators;
- determining, by the one or more processors, an integrated SNS risk score based on two or more of the plurality of SNS tone indicators and the respective weights;
- comparing, by the one or more processors, the integrated SNS risk score to a threshold SNS risk score; and
- determining, by the one or more processors, that the neuromodulation therapy was effective on the patient based on comparing the integrated SNS risk score to the threshold SNS risk score.

17. The method of claim 16, wherein determining that the neuromodulation therapy was effective on the patient comprises:
- determining, by the one or more processors, that the neuromodulation therapy was effective on the patient based on a determination that the integrated SNS risk score is greater than the threshold SNS risk score.

18. The method of claim 16, wherein comparing the integrated SNS risk score to the threshold SNS risk score comprises determining whether the integrated SNS risk score differs from the threshold SNS risk score, the method further comprising:
- providing, by the one or more processors, a recommendation to proceed with the neuromodulation therapy based on determining the integrated SNS risk score differs from the threshold SNS risk score.

19. The method of claim 16, wherein the plurality of SNS tone indicators comprises at least one of a heart rate variability (HRV), a night heart rate, an impedance variability, a net duration of atrial tachycardia (AT) or atrial fibrillation (AF), AT/AF burden, a patient activity level, or a day-night heart rate difference (DND).

* * * * *